United States Patent
Camino et al.

(10) Patent No.: US 11,302,043 B2
(45) Date of Patent: Apr. 12, 2022

(54) AUTOMATED DETECTION OF SHADOW ARTIFACTS IN OPTICAL COHERENCE TOMOGRAPHY ANGIOGRAPHY

(71) Applicant: Oregon Health & Science University, Portland, OR (US)

(72) Inventors: Acner Camino, Portland, OR (US); David Huang, Portland, OR (US); Yali Jia, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 225 days.

(21) Appl. No.: 16/803,629

(22) Filed: Feb. 27, 2020

(65) Prior Publication Data

US 2020/0273218 A1 Aug. 27, 2020

Related U.S. Application Data

(60) Provisional application No. 62/811,317, filed on Feb. 27, 2019.

(51) Int. Cl.
| | |
|---|---|
| *G06T 11/00* | (2006.01) |
| *A61B 3/10* | (2006.01) |
| *A61B 5/00* | (2006.01) |
| *G06T 7/00* | (2017.01) |
| *A61B 5/026* | (2006.01) |

(52) U.S. Cl.
CPC ............ *G06T 11/008* (2013.01); *A61B 3/102* (2013.01); *A61B 5/0261* (2013.01); *A61B 5/7203* (2013.01); *A61B 5/7264* (2013.01); *G06T 7/0016* (2013.01); *G06T 2207/10101* (2013.01); *G06T 2207/20081* (2013.01); *G06T 2207/30104* (2013.01); *G06T 2211/404* (2013.01)

(58) Field of Classification Search
CPC ..... G06T 5/005; G06T 11/005; G06T 11/008; G06T 7/0016; G06T 5/008; G06T 2207/20081; G06T 2207/30104; G06T 2207/10101; G06T 2211/404; G06T 2207/30041; A61B 5/7203; A61B 3/1225; A61B 5/0073; A61B 5/7264; A61B 5/0261; A61B 3/102
See application file for complete search history.

(56) References Cited

U.S. PATENT DOCUMENTS

| | | | |
|---|---|---|---|
| 10,402,965 B1 * | 9/2019 | Bagherinia | ........... G06T 7/0081 |
| 2018/0374213 A1 * | 12/2018 | Arnold | ................... G06T 7/0012 |
| 2019/0150764 A1 * | 5/2019 | Arnold | ................... G16H 15/00 |

* cited by examiner

*Primary Examiner* — Brenda C Bernardi
(74) *Attorney, Agent, or Firm* — Schwabe, Williamson & Wyatt, P.C.

(57) ABSTRACT

Disclosed herein are methods and systems for automated detection of shadow artifacts in optical coherence tomography (OCT) and/or OCT angiography (OCTA). The shadow detection includes applying a machine-learning algorithm to the OCT dataset and the OCTA dataset to detect one or more shadow artifacts in the sample. The machine-learning algorithm is trained with first training data from first training samples that include manufactured shadows and no perfusion defects and second training data from second training samples that include perfusion defects and no manufactured shadows. The shadow artifacts in the OCTA dataset and/or OCT dataset may be suppressed to generate a shadow-suppressed OCTA dataset and/or a shadow-suppressed OCT dataset, respectively. Other embodiments may be described and claimed.

22 Claims, 23 Drawing Sheets

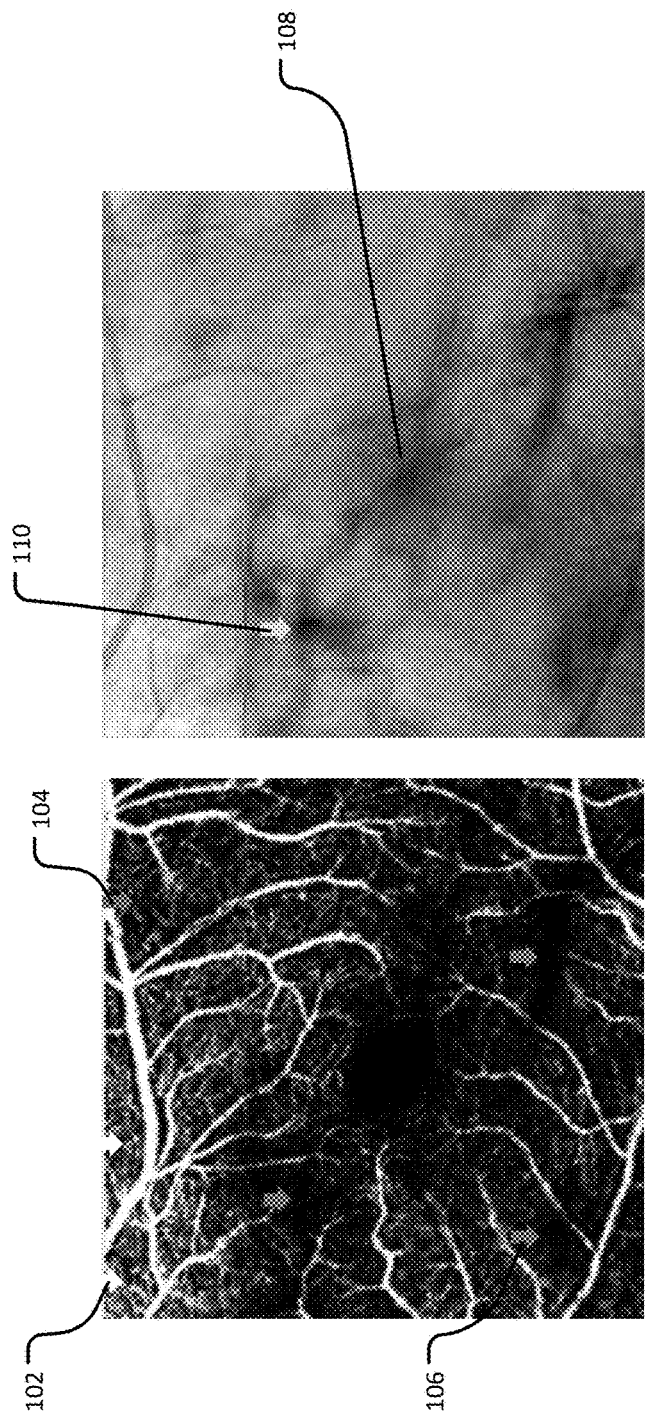
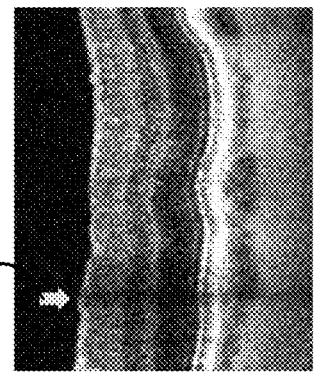
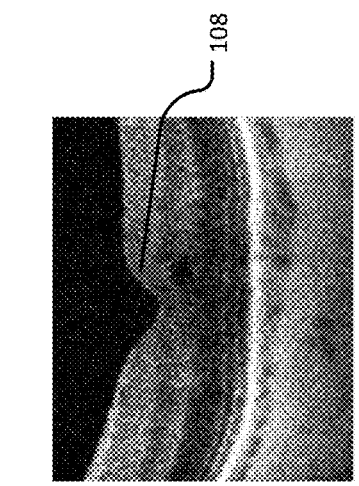
Figure 1A
Figure 1B
Figure 1C
Figure 1D

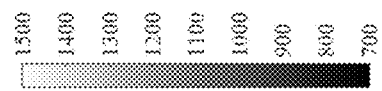 
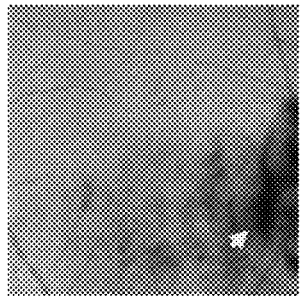 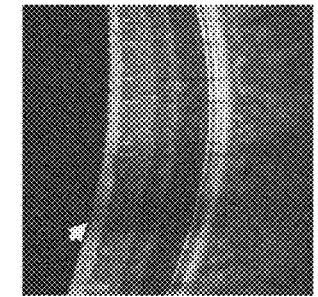 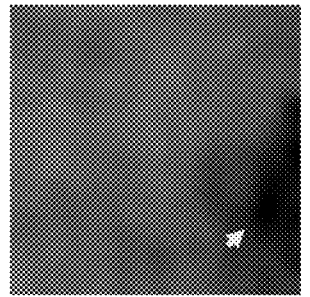
Figure 3A2 Figure 3B2 Figure 3C2
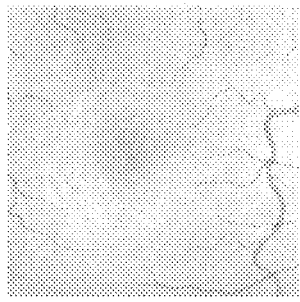 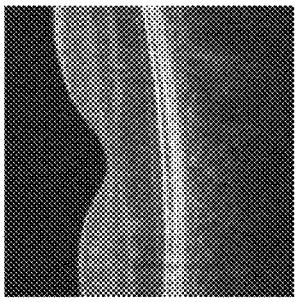 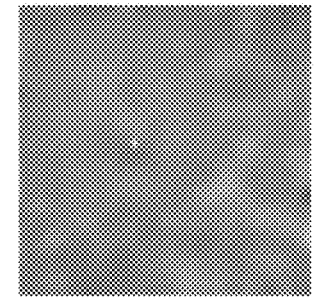
Figure 3A1 Figure 3B1 Figure 3C1

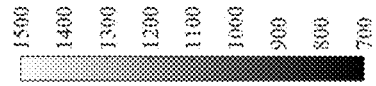
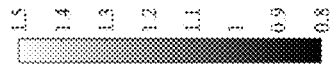
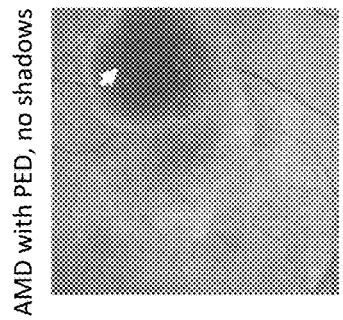
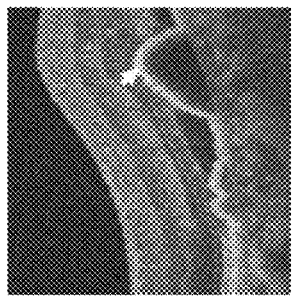
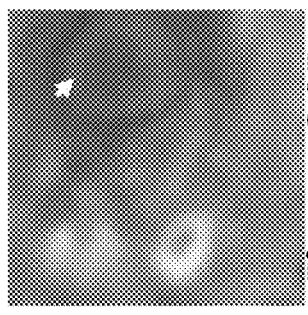
Figure 3A5    Figure 3B5    Figure 3C5
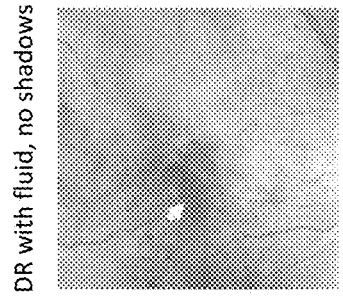
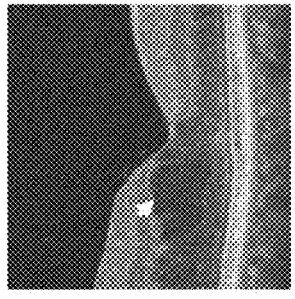
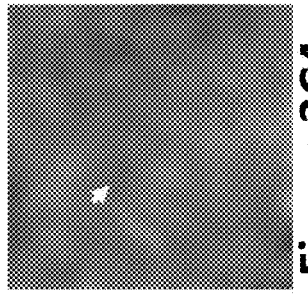
Figure 3A4    Figure 3B4    Figure 3C4
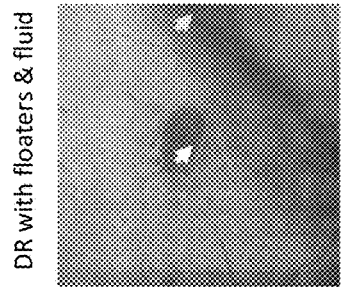
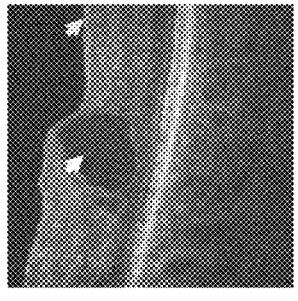
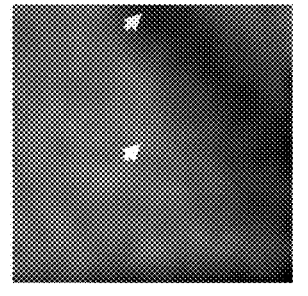
Figure 3A3    Figure 3B3    Figure 3C3

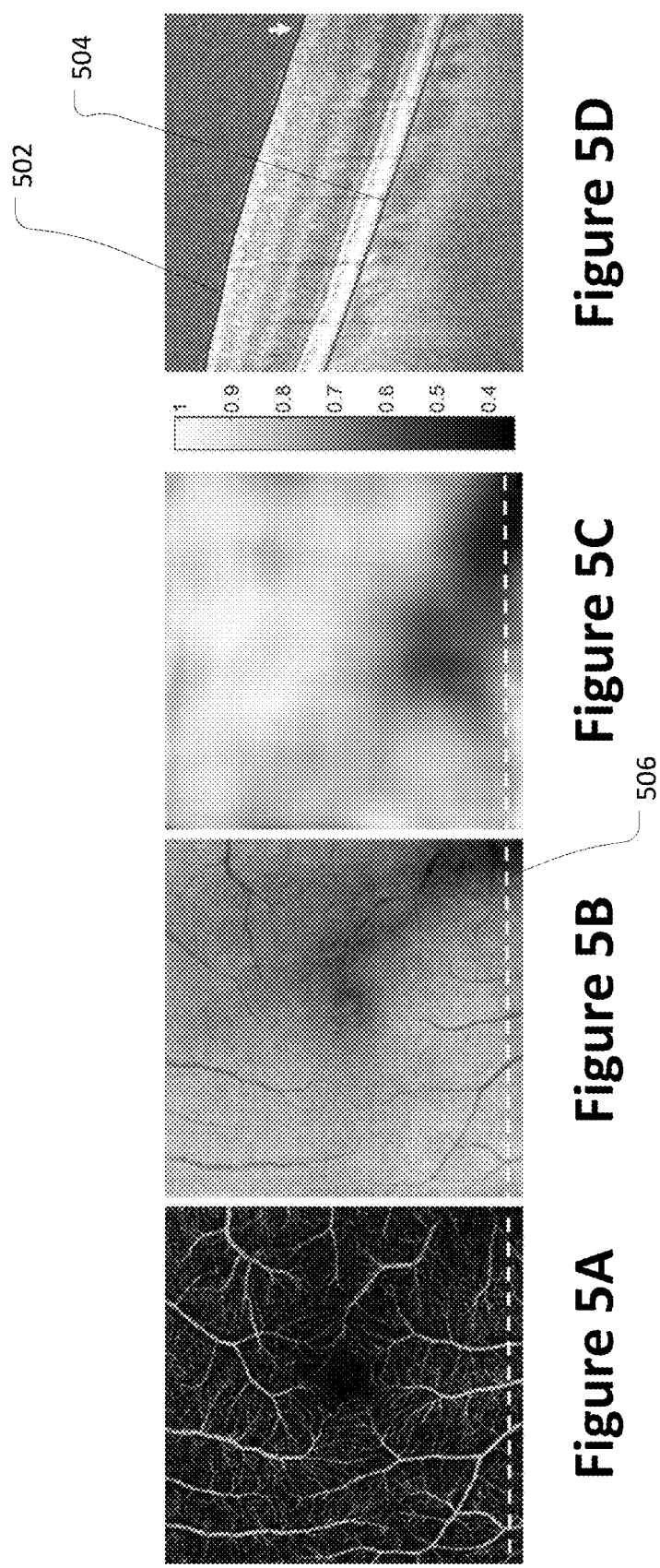

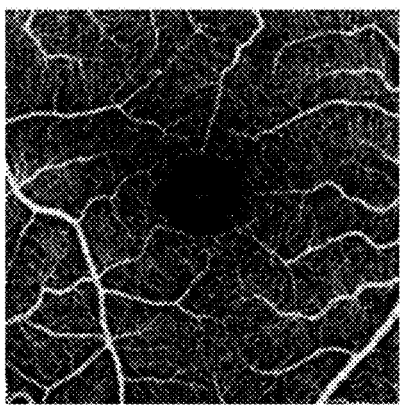
Figure 6A1
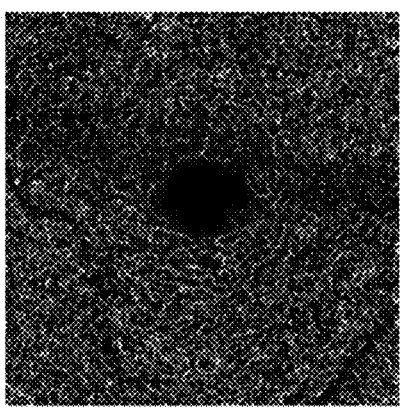
Figure 6B1
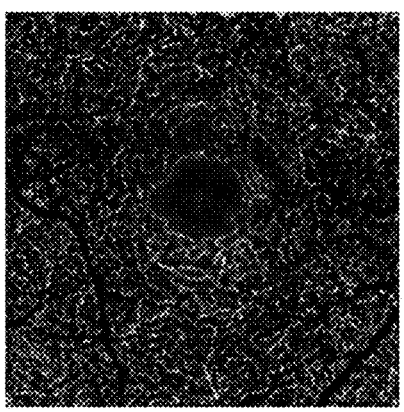
Figure 6C1
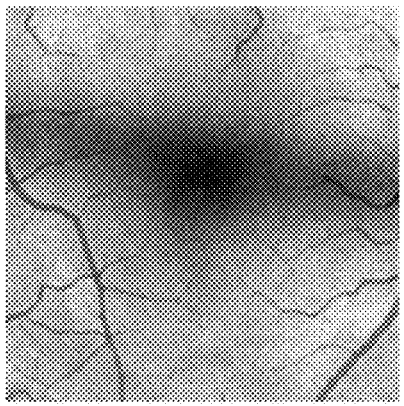
Figure 6D1
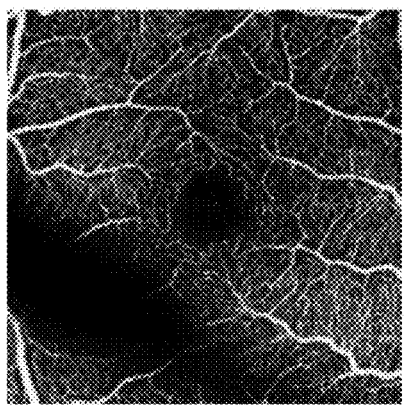
Figure 6A2
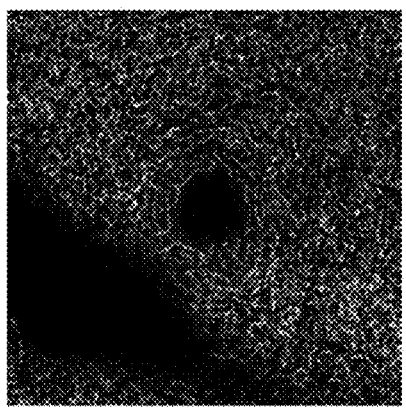
Figure 6B2
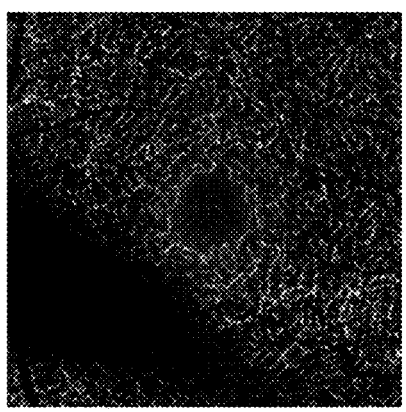
Figure 6C2
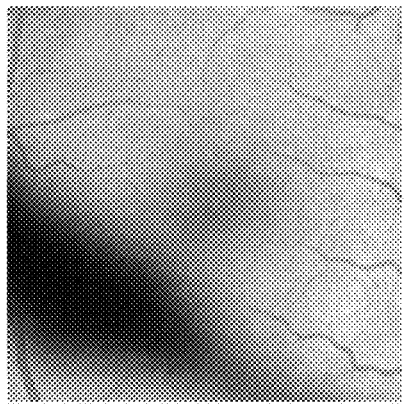
Figure 6D2

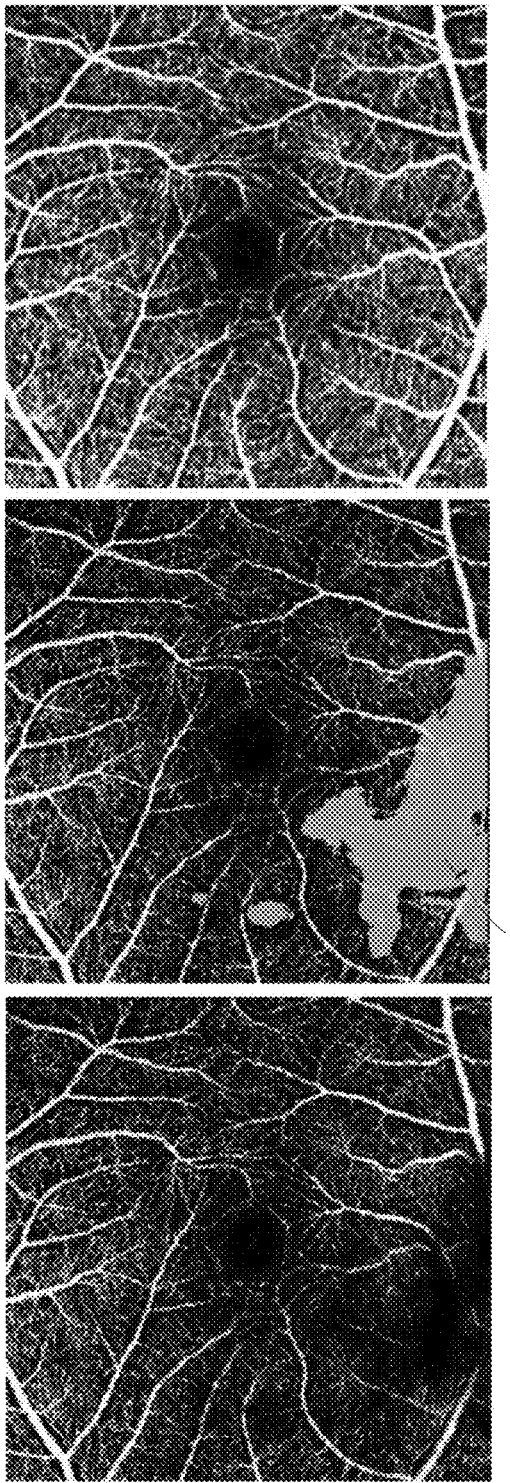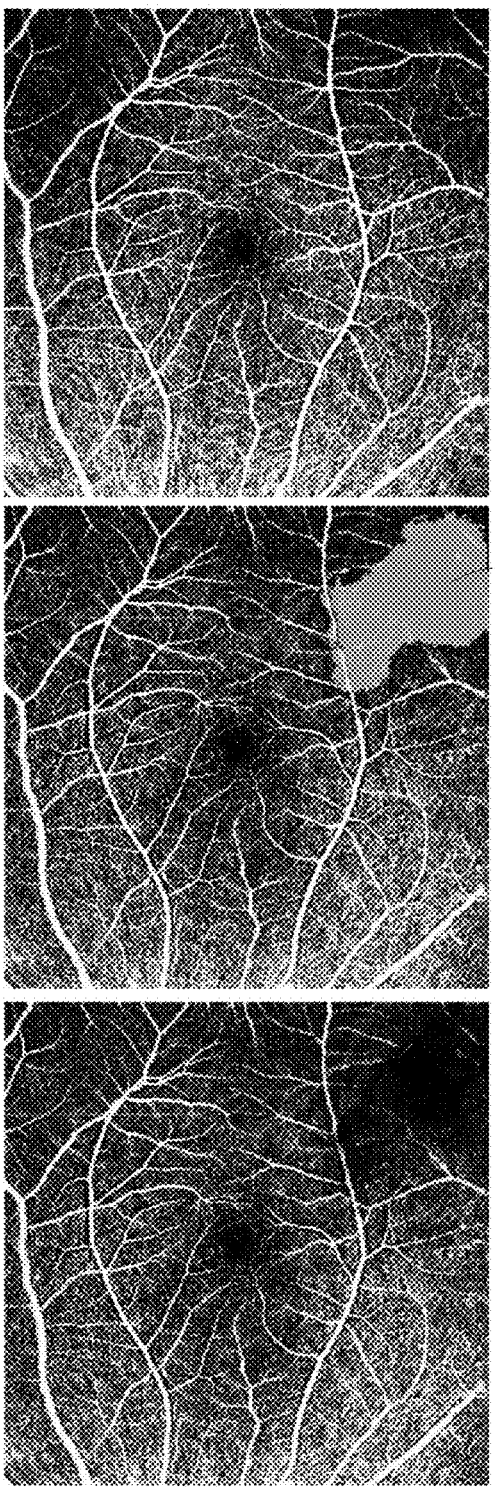
Figure 9A1, Figure 9B1, Figure 9C1, Figure 9A2, Figure 9B2, Figure 9C2

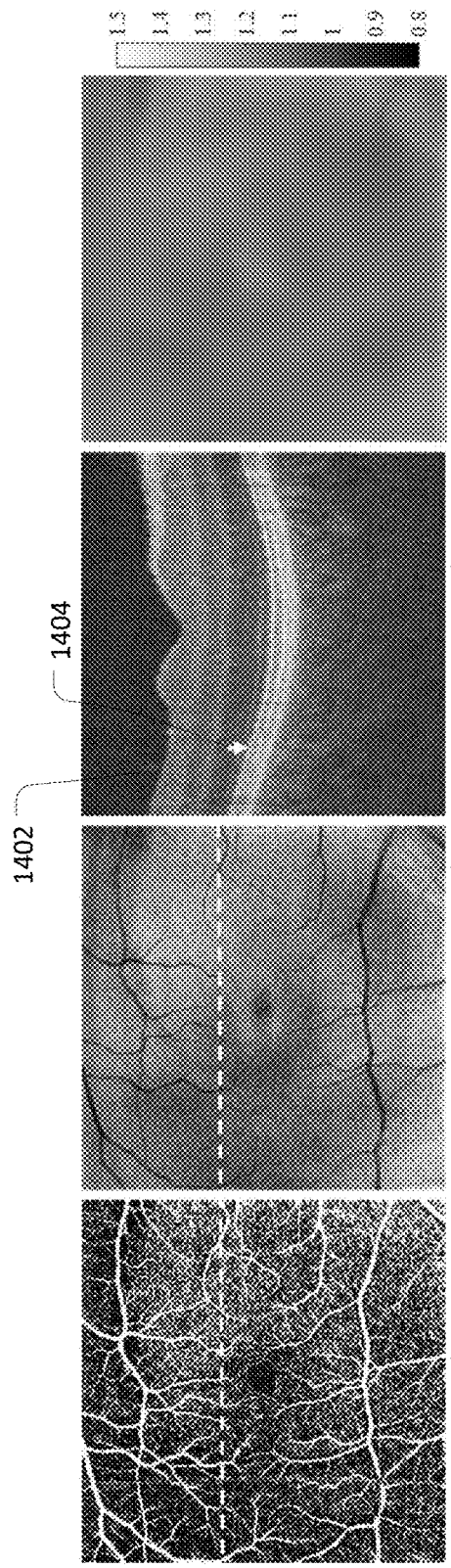
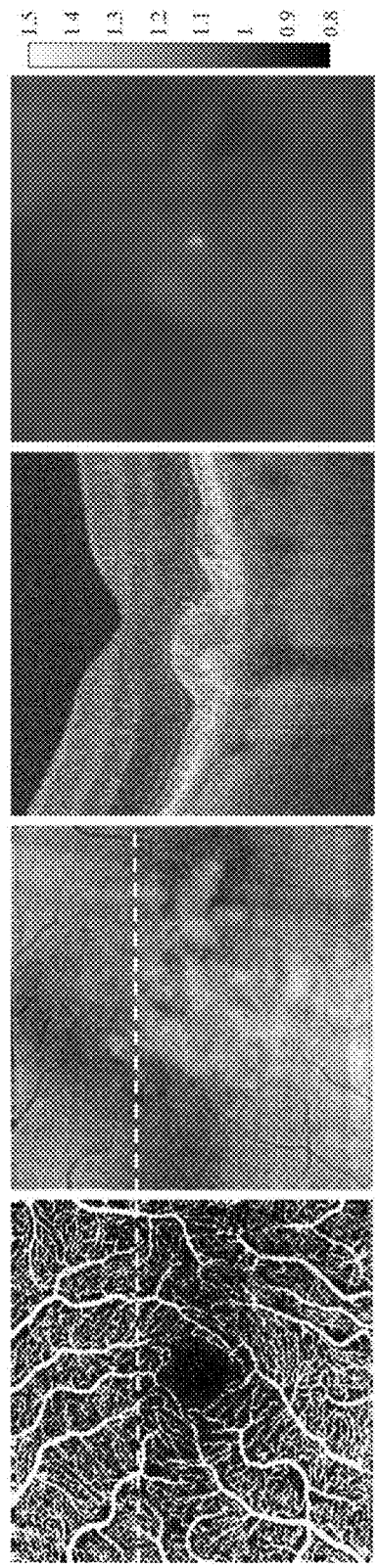

1502

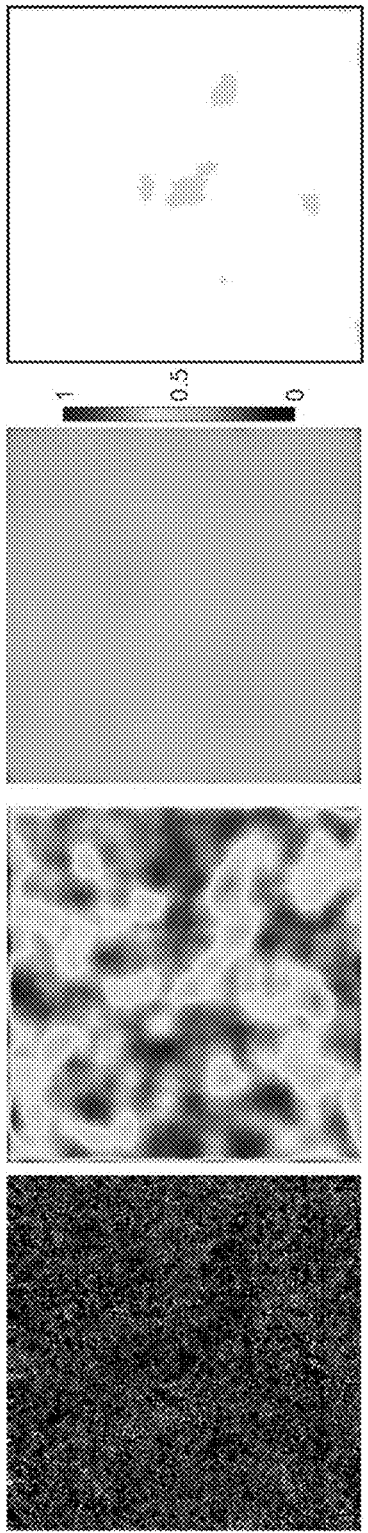
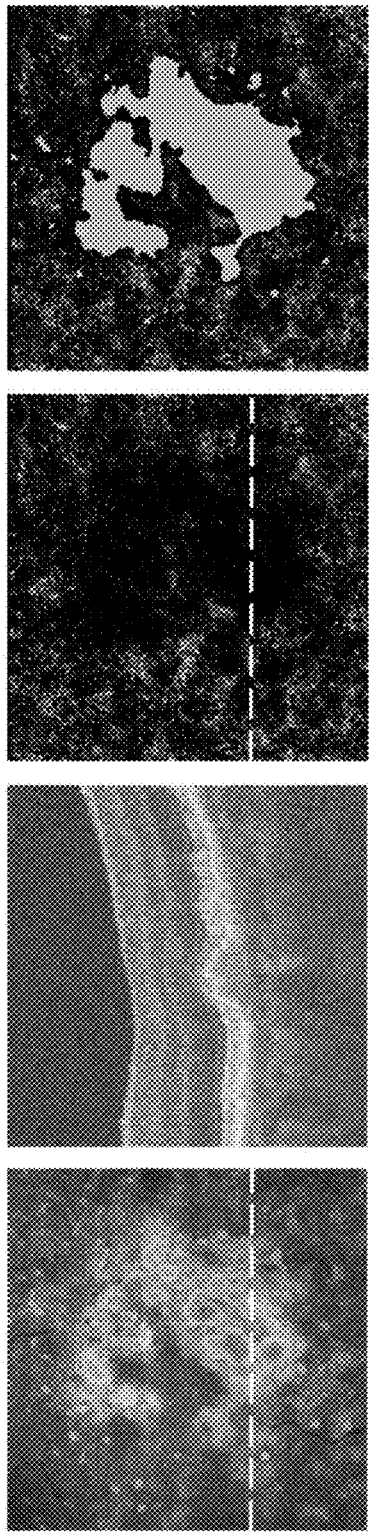

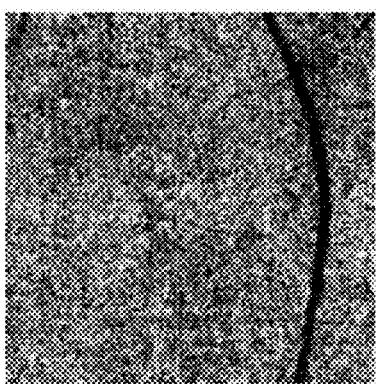 Figure 19A1
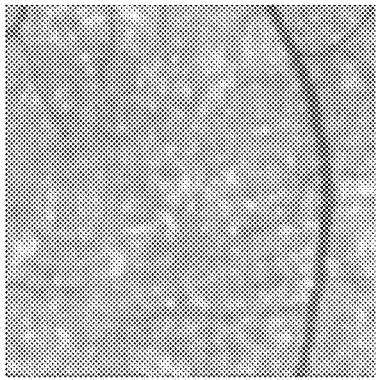 Figure 19B1
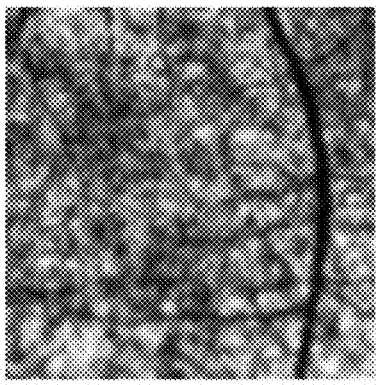 Figure 19C1
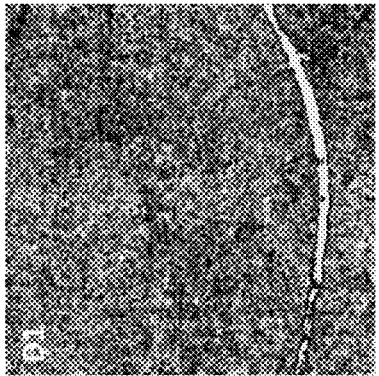 Figure 19D1
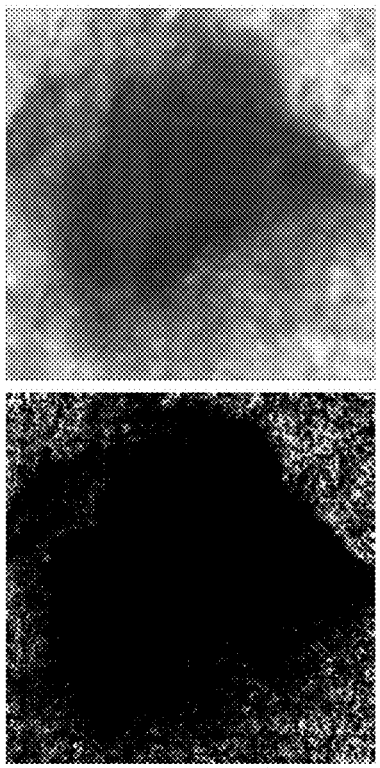 Figure 19A2
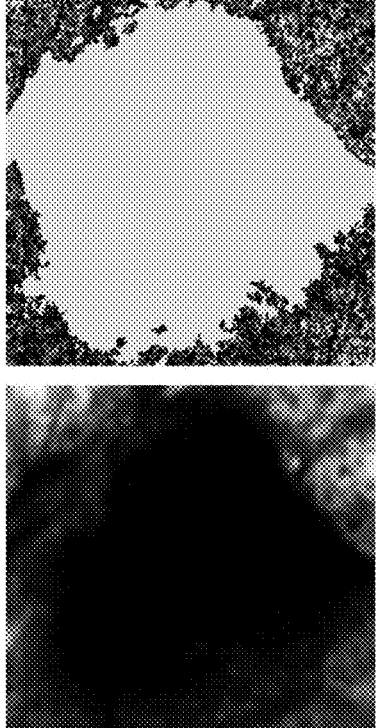 Figure 19B2
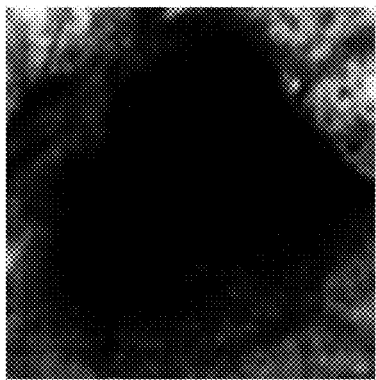 Figure 19C2
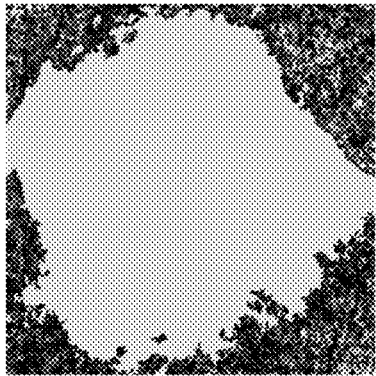 Figure 19D2

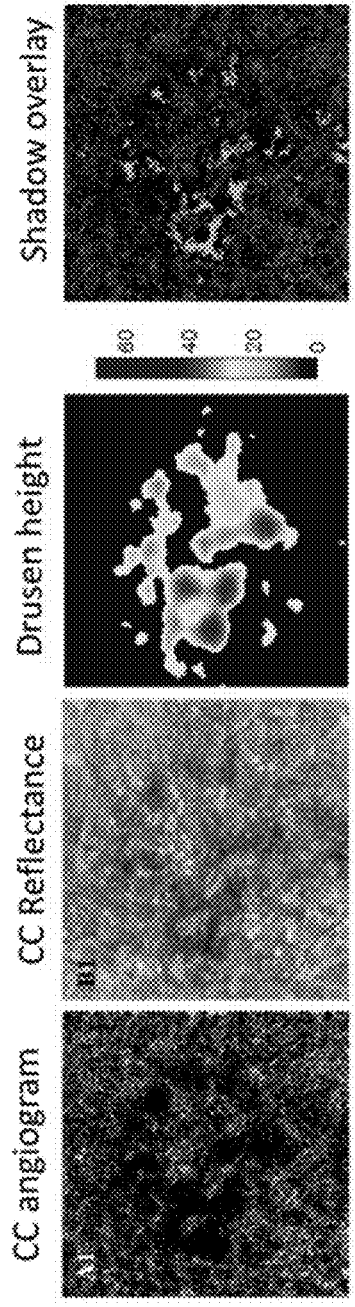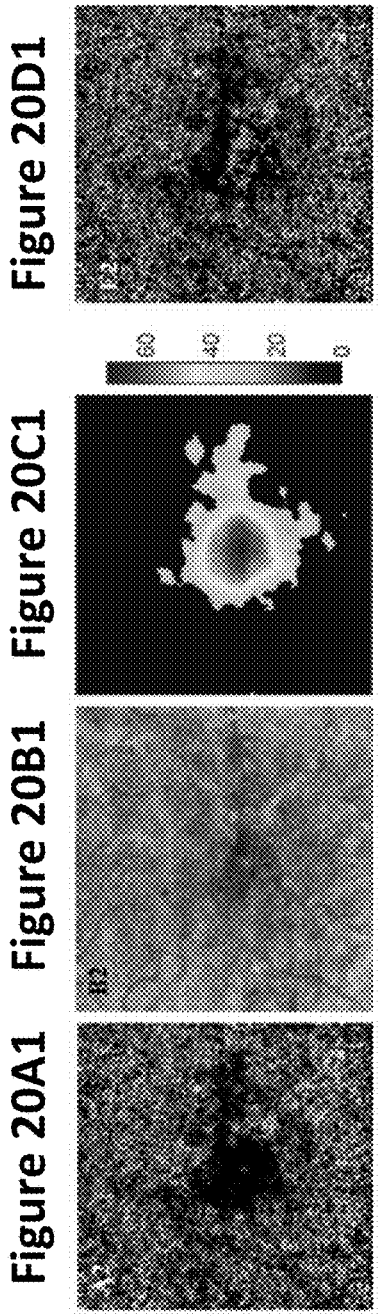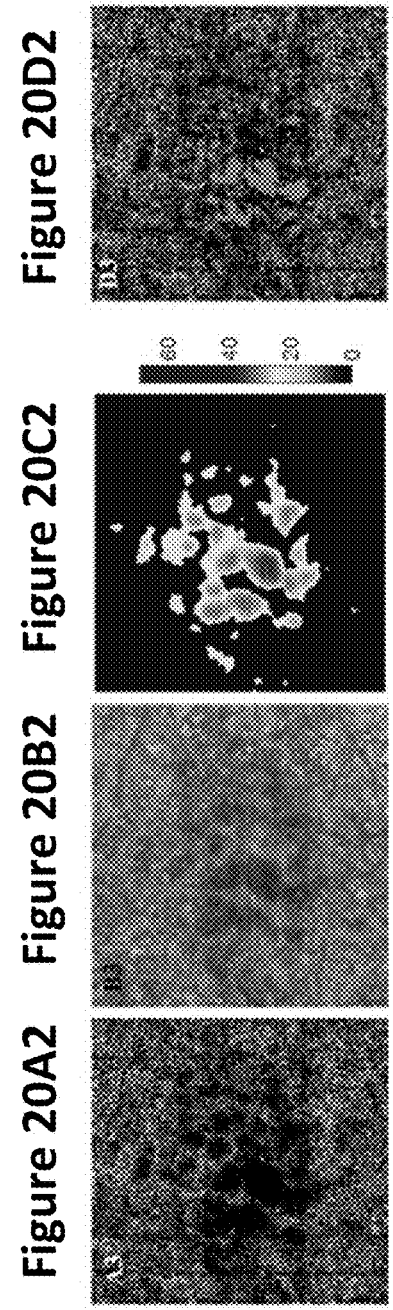

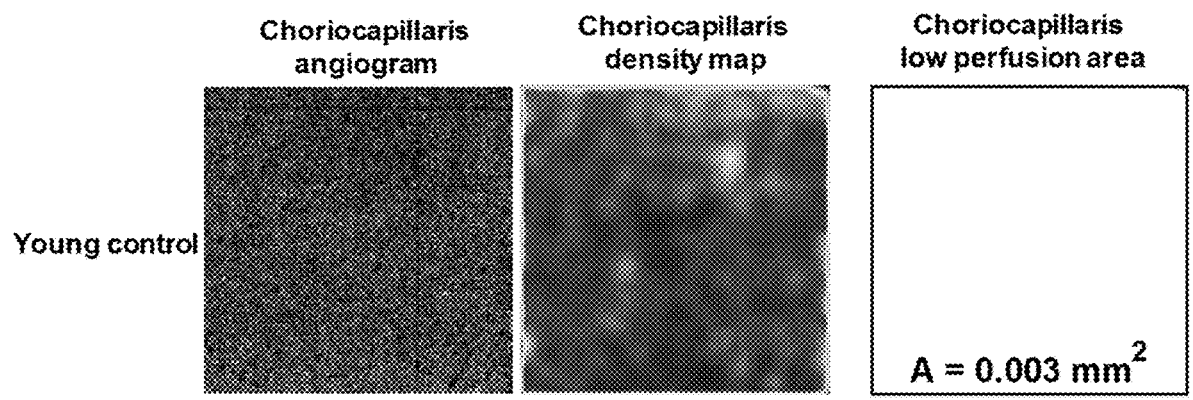
Figure 21A1  Figure 21B1  Figure 21C1
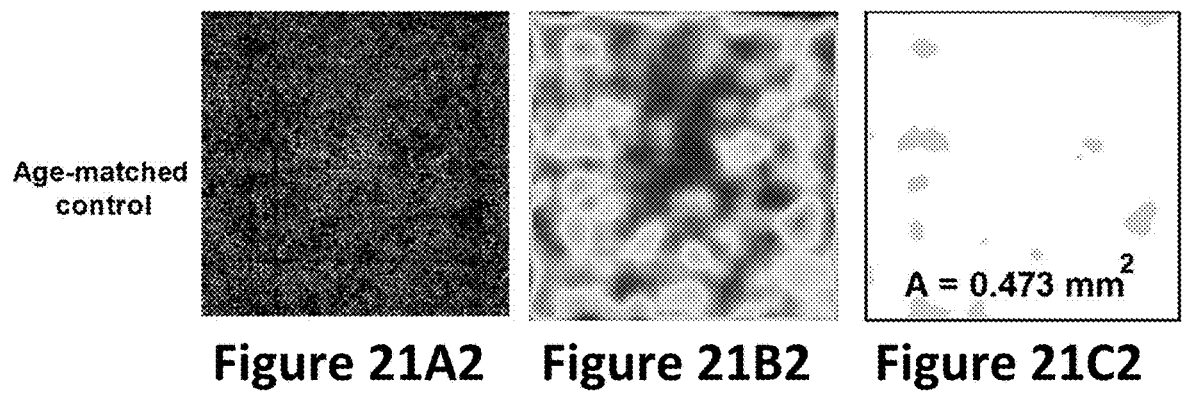
Figure 21A2  Figure 21B2  Figure 21C2
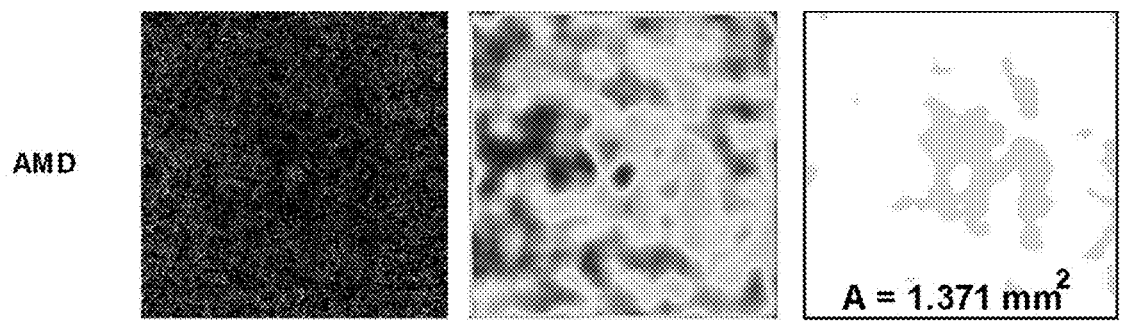
Figure 21A3  Figure 21B3  Figure 21C3

AUTOMATED DETECTION OF SHADOW ARTIFACTS IN OPTICAL COHERENCE TOMOGRAPHY ANGIOGRAPHY

CROSS REFERENCE TO RELATED APPLICATION

The present application claims priority to U.S. Provisional Patent Application No. 62/811,317, titled "AUTOMATED DETECTION OF SHADOW ARTIFACTS IN OPTICAL COHERENCE TOMOGRAPHY ANGIOGRAPHY," filed Feb. 27, 2019, the disclosure of which is hereby incorporated by reference in its entirety.

GOVERNMENT INTEREST STATEMENT

This invention was made with government support under R01 EY027833, DP3 DK104397, R01 EY024544, and R01 EY023285 from the National Institutes of Health. The government has certain rights in the invention.

FIELD

Generally, the field involves methods of imaging using optical coherence tomography. In particular, the field involves automated detection of shadow artifacts in optical coherence tomography angiography (OCTA).

BACKGROUND

Optical coherence tomography angiography (OCTA) is a non-invasive optical imaging modality for visualizing retinal circulation. It has emerged in recent years as an alternative to established technologies that require dye injection such as fluorescein angiography and indocyanine green angiography. Besides being fast and dye-free, other advantages of OCTA are depth-resolved visualization of retinal flow and superior representation of microvascular details. This last feature has allowed the development of analytical metrics with clinical application in detection of retinal vascular abnormalities. However, some of these metrics, such as vessel density or avascular area, may become unreliable if parts of the scan are blocked by vitreous floaters, by the pupil or by other opacities anterior to the retina.

OCTA commercial systems are generally equipped with software that analyzes the integrity of scans and computes a signal quality or signal strength index (SSI) to identify inadequate ones. The most common reasons for insufficient signal quality are excessive motion artifacts, poor beam focus, and media opacities (e.g. cataract). However, localized signal blockage by vitreous floaters or vignetting of a corner of the image by the pupil margin might not cause enough signal loss to deem the whole scan unsatisfactory. In such cases, shadows can be mistaken for focal perfusion loss in the clinical interpretation of the OCTA image and cause artefactual reduction in the overall vessel density or capillary density measured from the OCTA scan. Moreover, pupil vignetting and vitreous floaters are very common and difficult to avoid in OCTA images with larger fields of view. Therefore, it is preferable to identify and exclude these focal artifacts rather than discarding the entire scan.

Anterior segment and vitreous opacities affect both the reflectance and flow signals in the OCTA scan. The signal-processing problem of shadow detection can be described as follows. In en face OCTA images, shadowed areas appear dark (reduced flow signal), but they also appear dark in atrophied and ischemic areas. One may then turn to en face structural OCT images to distinguish shadows from perfusion defect. However en face structural OCT images are not reliable indicators of shadows either since atrophied and cystic areas also appear dark (see FIG. 1). The present inventors have previously described vascular pixel identification schemes that could compensate for partial shadowing by reflectance-adjusted thresholding. Other approaches have amplified the flow signal values under drusen shadows in order to retrieve some of the signal underneath. However, these methods fail in shadow areas with severe signal loss.

BRIEF DESCRIPTION OF THE SEVERAL VIEWS OF THE DRAWINGS

FIGS. 1A-1D Illustrate an image-processing problem while segmenting shadows caused by opacities anterior to the retina. FIG. 1A is an en face 3×3 mm² OCT angiogram of the superficial vascular complex of a patient with diabetic retinopathy (DR) containing vitreous floaters. Arrows 102 on the upper left corner represent areas of apparent normal perfusion. An arrow 104 represents the area of perfusion loss caused by the disease whereas arrows 106 represent loss of OCTA signal in shadowed areas. Because many diseases such as DR manifest real loss of perfusion, the loss of OCTA signal in FIG. 1A alone is not enough to discriminate regions shadowed by vitreous floaters. FIG. 1B is an en face mean projection of the retinal slab of the equivalent 3×3 mm² OCT reflectance image. FIG. 1C is a cross-sectional B-scan, and an arrow 108 represents an example of intra-retinal fluid that can cause dark areas in en face mean projections of OCT reflectance. FIG. 1D is another cross-sectional B-scan, and an arrow 110 illustrates an example of a dark area caused by a vitreous shadow.

FIG. 2A is a screenshot of the COOL ART user interface designed in MATLAB and used for retinal layer segmentation. The segmentation algorithm extracts the boundaries of multiple (e.g., eight) retinal layers from B-scans in the leftmost panel. Four en face panels represent the en face projections of OCTA and OCT information to facilitate fast and reliable interpretation of scans.

FIG. 2B illustrates a second pre-processing operation. The thresholding scheme in the rb-BMS algorithm removes background noise whereas preserving vascular information as observed in en face projections before (left) and after (right) thresholding. Arrows indicate cleanup of the noise in the normal foveal avascular zone. In some embodiments, no image filtering may be applied in rb-BMS.

FIGS. 3A1-3A5, 3B1-3B5, and 3C1-3C5 illustrate support for the rationale used in the selection of $R_{norm}$ (Eq. (3)) as a feature containing information of the positions of shadows. Columns represent scans from healthy (3A1-3C1 and 3A2-3C2, also referred to as subjects #1 and #2, respectively); diabetic retinopathy (DR, 3A3-3C3 and 3A4-3C4, also referred to as subjects #3 and #4, respectively) with intra-retinal fluid; and age-related macular degeneration (AMD) with pigment epithelium detachment (PED) subjects (3A5-3C5, also referred to as subject #5). Mean projection of the OCT reflectance within the retinal slab (FIGS. 3A1-3A5) frequently shows inhomogeneous brightness, containing dark areas caused by low internal reflectance (white arrows) such as intra-retinal fluid (subjects #3 and 4) and PED (subject #5). These need to be distinguished from true shadows such as those caused by vitreous opacities (indicated by arrows). FIGS. 3B1-3B5 show representative B-scans at the positions of arrows. The corresponding $R_{norm}$ images in FIGS. 3C1-3C5) are dark only when all retinal layers are dark, which corresponds better to actual shadows.

FIG. 4A illustrates an OCTA image of the superficial vascular complex (between ILM and 80% of the ganglion cell layer) of a patient with birdshot chorioretinopathy, a form of uveitis with characteristic abundance of vitreous floaters. FIG. 4B illustrates mean reflectance of the retinal slab between inner limiting membrane (boundary 402 in FIG. 4D) and Bruch's membrane (boundary 404 in FIG. 4D). FIG. 4C illustrates standard deviation of the reflectance in each A-line between the inner limiting membrane and the lower boundary of the choriocapillaris, normalized to the control group. FIG. 4D illustrates lower variation of the reflectance along the axial direction is appreciated (arrows 406) in a cross-sectional visualization of a B-scan affected by a shadow (dashed line 408).

FIGS. 5A-5D illustrate support for the rationale used in the definition of the local flow index, $FI_{focal}$, feature. FIG. 5A is an OCTA image of the superficial vascular complex of a patient with birdshot chorio-retinopathy. FIG. 5B depicts mean reflectance of the retinal slab between inner limiting membrane (boundary 502 in FIG. 5D) and Bruch's membrane (boundary 504 in FIG. 5D). Shadows are evident in the lower right corner of the scan. FIG. 5C depicts normalized inner-retinal local flow index (FI) map, where FI in the shadowed area is reduced to about 40% of the normal flow index at the respective positions. FIG. 5D illustrates a cross-sectional visualization of a B-scan affected by a shadow (dashed line).

FIGS. 6A1-6A2, 6B1-6B2, 6C1-6C2, and 6D1-6D2 illustrate images for which shadows were manufactured on healthy eyes by partially blocking the scanning beam with PLA filaments of different diameters (FIGS. 6A1-6D1 and FIGS. 6A2-6D2, respectively) and used to mimic clinical shadows in the training set of an ensemble classifier. FIGS. 6A1-6A2, 6B1-6B2, 6C1-6C2 show the en face projections of the superficial, intermediate and deep vascular plexuses found in the inner retina. FIGS. 6D1-6D2 show the en face projection of the OCT reflectance in the retinal slab.

FIG. 8A shows that the vessel density of the scans acquired without NDF is independent from signal strength index (SSI) after being processed by the reflectance-adjusted thresholding scheme in the regression-based bulk motion subtraction (rb-BMS) algorithm. FIG. 8B shows the vessel density of all scans acquired in this experiment, demonstrating that rb-BMS is not able to retrieve all signal after a certain level of attenuation. FIG. 8C depicts the vessel density of all scans in FIG. 8B by excluding the areas detected with the shadow segmentation algorithm. Note that by only considering the areas with reliable OCTA signal for quantification, the vessel density was again independent from SSI. FIG. 8D depicts the inverse linear relationship between shadow area and SSI in the NDF attenuation experiment, R=−0.67, p<0.01.

FIGS. 9A1, 9A2, 9B1, and 9B2 illustrate shadows from vitreous floaters on 3×3 mm² (9A1-9B1) and 6×6 mm² (9A2-9B2) macular OCTA scans of a healthy subject. Areas 902 overlapped onto en face projections of the superficial vascular complex represent the shadowed areas automatically detected by the algorithm. FIGS. 9C1-9C2 represent 3×3 mm² and 6×6 mm² OCTA, respectively, of the same subject after having the floaters removed in a vitrectomy. Floaters disappeared, revealing the intact vascular network on the superficial vascular complex. The vignette corner area in FIG. 9C2 is due to partial blockage of the optical signal by the pupil.

FIG. 12A shows regions of apparent loss of perfusion in en face view of the superficial vascular complex (center-left to lower-left corner). The white dashed line 1202 indicates the location of the cross-sectional view represented in FIG. 12B. The arrow 1204 identifies the presence of a shadow from vitreous floaters. Arrows 1206 indicate that the area exhibits increased optical signal penetration into the choroid caused by absence of retinal pigment epithelium. Shadows were nevertheless successfully detected as shown in FIG. 12C.

FIGS. 14A1, 14B1, 14C1, 14D1, 14A2, 14B2, 14C2, and 14D2 depict a demonstration of software performance in clinical cases with retinal degeneration and no vitreous floaters. Defects in the retina should not conduce to erroneous detection of shadows. FIGS. 14A1-14D1 show a scan from a patient with glaucoma exhibiting severe ganglion cell complex atrophy and FIGS. 14A2-14D2 show a scan from a patient with age-related macular degeneration (AMD) exhibiting severe outer-retina/choriocapillaris atrophy. FIGS. 14A1-14A2 are the respective 6×6 mm$^2$ and 3×3 mm$^2$ OCTA en face projections of the superficial vascular complex, showing perfusion loss caused by the disease in glaucoma and intact vasculature in AMD, since the inner retina is not affected. FIGS. 14B1-14B2 are the mean projection of the OCT reflectance within the retinal slab, showing dark areas in the atrophic areas. FIGS. 14C1-14C2 show cross-sectional views of B-scans of interest at positions marked with the dashed line. Arrows 1402 indicate regions of atrophy whereas white arrows 1404 indicate regions of non-degenerated or mildly affected retinal tissue. FIGS. 14D1-14D2 show the $R_{norm}$ maps corresponding to each case, in which the reflectance values are more homogeneous and above level of FIGS. 3C2-3C3, preventing the misclassification of the atrophic areas as vitreous shadows.

FIG. 15A is an en face projection of the superficial vascular complex containing large vessels that might cast shadows onto the choriocapillaris layer. As shown in FIG. 15B, the avascular voxels are set to zero by a reflectance-adjusted thresholding scheme in the regression-based bulk motion subtraction algorithm. The white square represents the kernel size used to generate density maps. FIG. 15C illustrates a density map generated by assigning to each pixel the local capillary density within the area enclosed by a moving window of size 10×10 pixels (white box 1502 in FIG. 15B). Areas underneath shadows cast by large vessels would exhibit artifactually reduced local vessel density if the shadowed pixels were not excluded. FIG. 15D illustrates the average of density maps from 40 scans on young, healthy eyes after registration to overlap their FAZ centers. FIG. 15E illustrates the standard deviation of 40 density maps from young, healthy eyes after registration to overlap their FAZ centers.

FIGS. 16A-16D illustrate apparent choriocapillaris low perfusion area detection from a subject in the age matched control group. FIG. 16A is an en face projection of choriocapillaris flow. FIG. 16B is a perfusion density map. FIG. 16C is a reference threshold map generated from young, healthy controls by $CC_{AVG}$ (x,y)−3.1×$CC_{STD}$ (x,y). FIG. 16D is a focal perfusion loss map generated by recognizing the positions of local capillary density values below threshold in FIG. 16C. The areas of apparent perfusion loss in FIG. 16D can be owing to either choriocapillaris dropout or flow signal loss in shadowed areas.

FIGS. 17A-17D illustrate automatic detection of drusen in eyes with dry age-related macular degeneration, in accordance with various embodiments. FIG. 17A is an en face projection of the OCT reflectance within a slab where drusen is found. FIG. 17B is a representative B-scan containing drusen, indicated by the position marked with white dashed lines. FIG. 17C illustrates a maximum projection of the flow within the choriocapillaris flow. FIG. 17D illustrates a drusen mask overlaid on the choriocapillaris angiogram.

FIGS. 19A1-19D1 and 19A2-19A2 illustrate two representative examples of shadow detection. FIGS. 19A1-19D1 are for a healthy subject. FIGS. 19A2-19D2 are for an age-related macular degeneration subject. FIGS. 19A1-19A2 are en face projections of the flow signal in the choriocapillaris slab showing significant absorption from a retinal vessel (19A1) and drusen (19A2), casting a shadow onto the choriocapillaris. FIGS. 19B1-19B2 illustrate corresponding mean reflectance projections of the choriocapillaris slab used as a feature to classify pixels as shadowed or not. FIGS. 19C1-19C2 illustrate corresponding en face maps of the background flow signal used as a feature to classify pixels as shadowed or not. FIGS. 19D1-19D2 illustrate results of the shadow detection overlaid on choriocapillaris angiogram.

FIGS. 20A1-20D1, 20A2-20D2, and 20A3-20D3 illustrate a comparison of the location of drusen areas vs shadow areas in three AMD subjects. FIGS. 20A1-20A3 show the en face OCTA image of the choriocapillaris layer and FIGS. 20B1-20B3 show the corresponding reflectance image. Both perfusion loss and preserved perfusion areas are apparent under drusen (see FIGS. 20C1-20C3). FIGS. 20D1-20D3 show the positions detected as unreliable, shadowed OCTA signal overlaid on the en face angiogram. These shadows were typically located at the positions of large drusen height.

FIGS. 21A1-21A3 illustrate choriocapillaris en face angiograms, FIGS. 21B1-21B3 illustrate density maps and FIGS. 21C1-21C3 illustrate low perfusion area of a young, healthy subject (FIGS. 21A1-21C1) a control subject from the group age-matched to the age-related macular degeneration (AMD) group (FIGS. 21A2-21C2) and a dry AMD subject (FIGS. 21A3-21C3). Low perfusion area of the AMD subject is represented after exclusion of shadow areas.

DETAILED DESCRIPTION

Figure 2A:
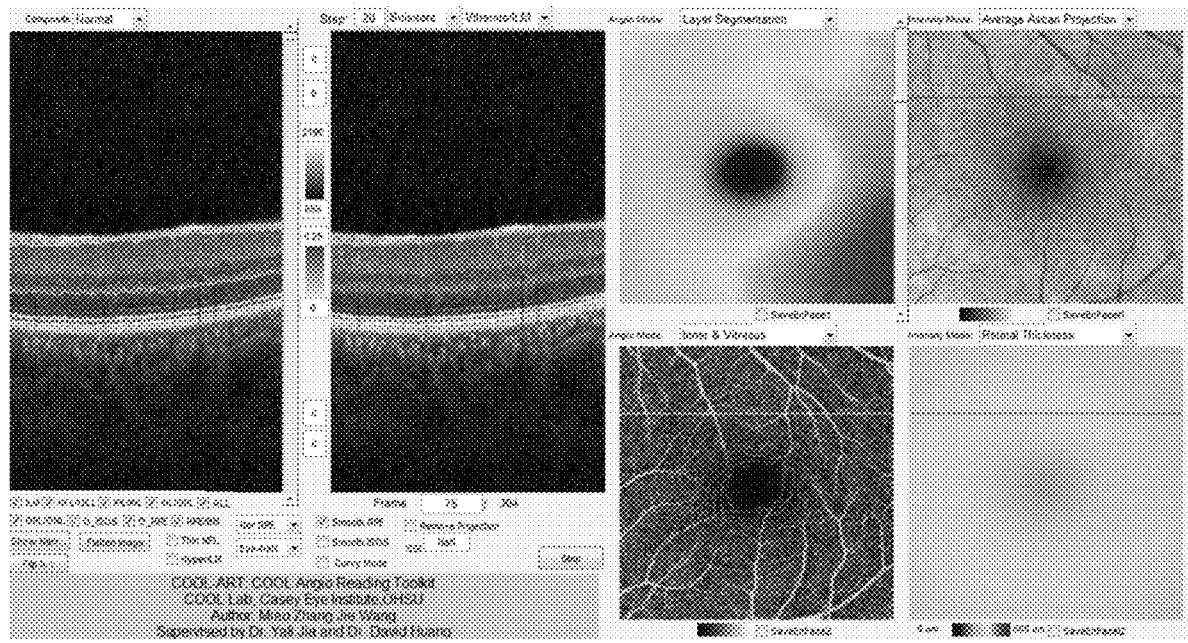
FIGS. 2A and 2B illustrate the OCTA signal pre-processing using a rb-BMS algorithm in accordance with some embodiments.

Disclosed herein are methods and systems for automated detection of shadow artifacts in optical coherence tomography (OCT) and/or OCT angiography (OCTA). The shadow detection includes applying a machine-learning algorithm to the OCT dataset and the OCTA dataset to detect one or more shadow artifacts in the sample. The machine-learning algorithm is trained with first training data from first training samples that include manufactured shadows and no perfusion defects and second training data from second training samples that include perfusion defects and no manufactured shadows. The shadow artifacts in the OCTA dataset and/or OCT dataset may be suppressed to generate a shadow-suppressed OCTA dataset and/or a shadow-suppressed OCT dataset, respectively. Also disclosed herein is an exemplary system for acquiring and/or processing OCT/OCTA images. The exemplary system comprises an OCT device configured to acquire OCT structural and angiography data in functional connection with a computing device having a logic subsystem and data holding capabilities. In embodiments the computing device is configured to receive data from the OCT device and perform one or more operations of the methods described herein.

In the following detailed description, reference is made to the accompanying drawings which form a part hereof, and in which are shown by way of illustration embodiments that can be practiced. It is to be understood that other embodiments can be utilized and structural or logical changes can be made without departing from the scope. Therefore, the following detailed description is not to be taken in a limiting sense, and the scope of embodiments is defined by the appended claims and their equivalents.

Various operations can be described as multiple discrete operations in turn, in a manner that can be helpful in understanding embodiments; however, the order of description should not be construed to imply that these operations are order dependent.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, structure and/or flow information of a sample can be obtained using OCT (structure) and OCT angiography (flow) imaging-based on the detection of spectral interference. Such imaging can be two-dimensional (2-D) or three-dimensional (3-D), depending on the application. Structural imaging can be of an extended depth range relative to prior art methods, and flow imaging can be performed in real time. One or both of structural imaging and flow imaging as disclosed herein can be enlisted for producing 2-D or 3-D images.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

In order to facilitate review of the various embodiments of the disclosure, the following explanation of specific terms is provided:

A-scan: A reflectivity profile that contains information about spatial dimensions and location of structures within an item of interest. An A-scan is an axial scan directed along the optical axis of the OCT device and penetrates the sample being imaged. The A-scan encodes reflectivity information (for example, signal intensity) as a function of depth (z-direction).

B-scan: A cross-sectional tomograph that can be achieved by laterally combining a series of axial depth scans (i.e., A-scans) in the x-direction or y-direction. A B-scan encodes planar cross-sectional information from the sample and is typically presented as an image. Thus, a B-scan can be called a cross sectional image. The axis orthogonal to the A-scan axis in the plane of the cross-sectional scanning location of the B-scan is referred to as the fast axis. Accordingly, the scanner travels along the fast axis while obtaining A-scans that are combined to form one B-scan. The axis orthogonal to the plane of the cross-sectional scanning location of the B-scan is referred to as the slow axis.

Dataset: As used herein, a dataset is an ordered-array representation of stored data values that encodes relative spatial location in row-column-depth (x-y-z axes) format. In the context of OCT, as used herein, a dataset can be conceptualized as a three dimensional array of voxels, each voxel having an associated value (for example, an intensity value, a complex value having both amplitude and phase information, a decorrelation value, or other signal representations). An A-scan corresponds to a set of collinear voxels along the depth (z-axis) direction of the dataset; a B-scan is made up of set of adjacent A-scans combined in the row or column (x- or y-axis) directions. Such a B-scan can also be referred to as an image, and its constituent voxels referred to as pixels. A collection of adjacent B-scans can be combined form a 3D volumetric set of voxel data referred to as a 3D image. In the system and methods described herein, the dataset obtained by an OCT scanning device is termed a "structural OCT" dataset whose values can, for example, be complex numbers carrying intensity and phase information. This structural OCT dataset can be used to calculate a corresponding dataset termed an "OCT angiography" dataset reflecting flow within the imaged sample. There is a correspondence between the voxels of the structural OCT dataset and the OCT angiography dataset. Thus, values from the datasets can be "overlaid" to present composite images of structure and flow (e.g., tissue microstructure and blood flow) or otherwise combined or compared.

En Face angiogram: OCT angiography data can be presented as a 2D projection of the three dimensional dataset onto a single planar image called an en face angiogram. Construction of such an en face angiogram requires the specification of the upper and lower depth extents that enclose the region of interest within the retina OCT scan to be projected onto the angiogram image. These upper and lower depth extents can be specified as the boundaries between different layers of the retina (e.g., the voxels between the inner limiting membrane and outer plexiform layer could be used to generate an en face angiogram of the inner retina). Once generated, the en face angiogram image may be used to quantify various features of the retinal vasculature as described herein. This quantification typically involves the setting of a threshold value to differentiate, for example, the pixels that represent flow within vasculature from static tissue within the angiogram. These en face angiograms can be interpreted in a manner similar to traditional angiography techniques such as fluorescein angiography (FA) or indocyanine green (ICG) angiography, and are thus well-suited for clinical use. It is also common to generate en face images from structural OCT data in a manner analogous to that used to generate en face angiograms. Angiograms from different layers may also be color-coded and overlaid to present composite angiograms with encoded depth information; structural en face images may also be included in such composite image generation.

Functional OCT, as used herein, broadly refers to the extension of OCT techniques to provide information beyond structural characterization. For example, whereas structural OCT imaging may be used to gather spatial information about a tissue's anatomical organization, functional OCT may be used to gather information about processes occurring within that tissue sample such as blood flow, tissue perfusion and oxygenation, birefringence, etc. Examples of functional OCT include, but are not limited to, OCT angiography (OCTA) and associated techniques for characterizing blood flow, Doppler OCT, polarization-sensitive OCT, OCT elastography, spectroscopic OCT, differential absorption OCT, and molecular imaging OCT.

FIGS. 1A-1D Illustrate the image-processing problem while segmenting shadows caused by opacities anterior to the retina. FIG. 1A is an en face 3×3 mm$^2$ OCT angiogram of the superficial vascular complex of a patient with diabetic retinopathy (DR) containing vitreous floaters. Arrows 102 on the upper left corner represent areas of apparent normal perfusion. An arrow 104 represents the area of perfusion loss caused by the disease whereas arrows 106 represent loss of OCTA signal in shadowed areas. Because many diseases such as DR manifest real loss of perfusion, the loss of OCTA signal in FIG. 1A alone is not enough to discriminate regions shadowed by vitreous floaters. FIG. 1B is an en face mean projection of the retinal slab of the equivalent 3×3 mm$^2$ OCT reflectance image. An arrow 108 represents an example of intra-retinal fluid (see cross-sectional B-scan in FIG. 1C) that can cause dark areas in en face mean projections of OCT reflectance. An arrow 110 illustrates an example of a dark area caused by a vitreous shadow (see cross-sectional B-scan in FIG. 1D). There is a need to distinguish true perfusion loss (arrow 104) from shadowing (arrows 106) by analyzing tissue reflectance, but without falsely excluding areas of low tissue reflectivity such as fluid space (arrow 108). An insight that applies to various embodiments herein is that true shadowing affects reflectance signal throughout the entire image depth (arrow 110 in FIG. 1D), while low tissue reflectivity such as cysts are confined to a single layer (arrow 108 in FIG. 1C).

Various embodiments provide an algorithm that discriminates areas where the absence of flow signal is due to actual physiological processes associated with retinal disease rather than artefactual shadows. The algorithm is calibrated with a training data set for which manufactured shadows are created by partially blocking the optical signal in the sample arm of the OCT instrument (e.g., with opaque filaments of polylactic acid (PLA)). In various embodiments, features of shadow pixels are identified based on OCT reflectance and/or OCTA focal perfusion density and/or flow index in order to train an ensemble classifier that identified the normal from shadow pixels in the feature space of principal components. As described further below, the algorithm was validated by scanning healthy subjects with progressively increasing signal attenuation using neutral density filters (NDF) between the eye and the instrument. Since NDFs were manufactured using a Schott glass substrate that reduces the intensity reaching the retina by different optical densities, their effect on signal strength can simulate that of cataracts attenuating light by multiple scattering in the nucleus of the crystalline lens. The algorithm was also tested on healthy subjects with natural floater shadows and pupil vignetting, as well as on patients with diabetic retinopathy (DR), uveitis, age-related macular degeneration (AMD) and glaucoma.

Various aspects of the disclosed techniques are described in more detail below. For example, a system configuration for automated detection of shadow artifacts in OCTA is shown and described. In an aspect, a machine-learning algorithm may be applied to an OCTA dataset and/or an OCT dataset to detect shadow artifacts. The machine-learning algorithm may distinguish between shadow artifacts and perfusion defects in the sample (e.g., retina and/or choriocapillaris).

Quantification of retinal perfusion by OCTA has clinical utility. Based on OCTA images alone, shadows are indistinguishable from defects in ocular perfusion. Thus, detecting these artifacts is important in the measurement of vascular density and perfusion defects. If shadows are not accounted for, the accuracy of quantified perfusion of one or many plexuses might be compromised owing to areas of unreliable OCTA signal masquerading as perfusion loss. The present inventors have previously described vascular pixel identification schemes that could compensate for partial shadowing by reflectance-adjusted thresholding. However, these methods fail in shadow areas with severe signal loss.

The techniques described herein detect regions of unreliable OCTA signal in shadowed areas. The techniques may be employed for retinal tissue, choriocapillaris tissue, and/or other suitable tissue. In the choriocapillaris embodiment, shadows caused by opacities located at the retina such as drusen and large vessels may be excluded in addition to the opacities anterior to the retina.

In various embodiments, a machine-learning algorithm may be applied to OCTA and/or OCT datasets to detect shadows. The algorithm may detect the regions of the OCTA and/or OCT data that are affected by shadow defects. In some embodiments, the algorithm may suppress the detected shadow defects from the OCTA dataset to generate a shadow-suppressed OCTA dataset. For example, the algorithm may mark the detected shadow regions for exclusion from the quantification of OCTA metrics, thereby improving the accuracy and reliability of the metrics.

In various embodiments, the supervised machine learning method may be trained on training data from healthy subjects scanned in conditions that create manufactured shadows. This experimental procedure allowed to generate a reliable training dataset with accurate labels assigned to shadowed vs non-shadowed pixels, which is critical for an optimal training of the algorithm. In some embodiments, scans of subjects with perfusion loss but no shadowing may be included in the training data set, thereby avoiding false classification of retinal atrophy as shadow areas.

In various embodiments, the algorithm described herein may not rely on the contrast between the pixels on the sides of shadow boundaries, but rather on the characteristics of shadowed A-lines. This means that in principle, in a scan significantly below the required minimum quality index (e.g. a patient with severe cataracts), a large area could be potentially detected as a shadow, independently of whether floaters and vignetting exist or not. The accuracy of this classification was demonstrated by an experiment in which signal strength was attenuated externally by neutral density filters on OCTA of healthy subjects, as further discussed below.

Example OCT System

The techniques described herein may be implemented on any suitable OCT system and/or data acquisition settings. In the example experiments described herein, subjects were scanned with a commercial, 840-nm-wavelength, 70-kHz spectral-domain OCT system (Avanti RTVue-XR, Optovue Inc.) using AngioVue 3×3 and 6×6 mm$^2$ OCTA scan patterns. Tracking was activated to reduce motion artifacts. The 3×3 mm$^2$ scans contained volumetric data at 304×304 A-lines. The 6×6 mm$^2$ scans used the AngioVue high-definition (HD) format, which contains 400×400 A-lines. Flow signal was generated by the split-spectrum amplitude-decorrelation (SSADA) algorithm (e.g., as described in Y. Jia, O. Tan, J. Tokayer, B. Potsaid, Y. Wang, J. J. Liu, M. F. Kraus, H. Subhash, J. G. Fujimoto, J. Hornegger, and D. Huang, "Split-spectrum amplitude-decorrelation angiography with optical coherence tomography," Opt Express 20, 4710-4725 (2012); and/or Y. Jia, S. T. Bailey, T. S. Hwang, S. M. McClintic, S. S. Gao, M. E. Pennesi, C. J. Flaxel, A. K. Lauer, D. J. Wilson, J. Hornegger, J. G. Fujimoto, and D. Huang, "Quantitative optical coherence tomography angiography of vascular abnormalities in the living human eye," Proceedings of the National Academy of Sciences 112, E2395 (2015); both of which are incorporated by reference herein) from two repeated B-scans at each lateral position. An orthogonal registration algorithm (e.g., as described in M. F. Kraus, B. Potsaid, M. A. Mayer, R. Bock, B. Baumann, J. J. Liu, J. Hornegger, and J. G. Fujimoto, "Motion correction in optical coherence tomography volumes on a per A-scan basis using orthogonal scan patterns," Biomed Opt Express 3, 1182-1199 (2012), herein incorporated by reference) was used to merge two raster scans—one with horizontal-priority and one with vertical-priority. This algorithm was originally developed by Massachusetts Institute of Technology (MIT), and implemented by Optovue as their proprietary Motion Correction Technology (MCT) software. The merged volumetric OCTA scan contain both structural (reflectance) and angiographic (flow) data that is further analyzed. The merged volume will be referred to as a "scan" in this disclosure.

Training Data

In various embodiments, the machine-learning algorithm described herein may be trained using training data. The training data may include a first set of training data from healthy subjects/samples with manufactured shadows. In some embodiments, the training data may further include a second set of training data from subjects/samples with perfusion defects but no shadows.

For example, for purposes of the machine-learning algorithm used for the experiments described further below, eight scans of varying signal strength were obtained from one eye of each healthy subject. A first scan was acquired under optimal imaging conditions. Then six increasingly attenuated scans were acquired by placing different combinations of NDFs between the eye and the scanner, achieving various degrees of global attenuation with local effects in the OCTA signal retrieved. No physical compensation of the dispersion mismatch introduced by the glass could be done in the reference arm of the commercial OCT system, thus relying on the automatic numerical compensation by AngioVue's software. A final unattenuated scan was acquired for repeatability assessment.

Scans with manufactured shadows were obtained from one eye of ten healthy subjects. Two scans were first obtained under optimized imaging conditions from each eye. Then a scan with a focal shadow was obtained from each eye. The shadow was produced by placing a filament of PLA between the eye and the scanning optics in the sample arm of the instrument, avoiding the foveal avascular zone.

Scans were also obtained from clinical research participants with known eye conditions. Two scans were obtained from one eye of these subjects. All participants were recruited from the Casey Eye Institute at the Oregon Health & Science University (OHSU). These scans may contain focal shadows, but must pass quality assessment to assure good focus, no excessive motion artifacts, and Q-score of at least 6 as assessed by AngioVue software version 2017.1.0.151. The protocol was approved by the Institutional Review Board/Ethics Committee of OHSU and the research adhered to the tenants of the Declaration of Helsinki.

It will be apparent that modifications to the training data and/or acquisition thereof may be made within the scope of the present disclosure.

Considerations on Discrimination of Flow Vs. Background Signal in OCTA OCTA algorithms detect flow signal at each voxel (x, y, z) by computing motion-associated changes of the OCT reflectance signal expressed as $A(x, y, z; t_m) = A_0(x, y, z; t_m) \exp[i\Phi(x, y, z; t_m)]$ in MB-scans (a set of multiple B-scans) of the same tissue section. One early approach to tackle this task was to compute the variance of the phase $\Phi$ or the speckle amplitude $A_0$ to gain contrast between static tissue and flow voxels (with high signal variance). However, as OCTA developed, these algorithms had to adapt to two major problems.

The first problem was that speckle variance increased with reflectance signal strength, thus yielding larger flow signal in tissue layers with strong reflectivity, as well as blood vessels. To highlight flow and reduce the influence of signal strength and tissue reflectivity, normalization was needed. One way to normalize signal strength is to divide speckle variance by the summation of the signal strengths squared, yielding a quantity called decorrelation (Eq. 1). Alternatively, the ratio between sequential signal amplitude can be evaluated, which is equivalent to taking the variance of logarithmic amplitude rather than the linear amplitude. Mathematically, all of these quantities—decorrelation, amplitude ratio, and phase variance—are measures of variation nominally unaffected by the average reflectance amplitude.

$$D(x, z) = 1 - \frac{1}{M-1} \sum_{m=1}^{M-1} \frac{A_0(x, z; t_m) A_0(x, z; t_{m+1})}{\frac{1}{2}(A_0(x, z; t_m)^2 + A_0(x, z; t_{m+1})^2)} \quad (1)$$

However, all of these OCTA algorithms still need to take steps to eliminate the contribution from noise. Since a series of pure noise is maximally decorrelated, voxels where noise predominate over signal could be mistaken as flow voxels. For amplitude-based algorithms such as split-spectrum amplitude decorrelation angiography (SSADA), a floor can be placed on the OCT signal amplitude so that voxels with very low signal also have very low decorrelation and logarithmic variance. For phase-based algorithms, the phase can be excluded from analysis if the magnitude falls below a threshold. Unfortunately, the noise-filtering step re-introduces a signal strength dependence to quantification of metrics with clinical utility derived from flow signal. As reflectance signal drops, both flow signal and noise are increasingly filtered out. The present inventors have found empirically that the vessel density—measured as the percentage of vascular pixels—scales approximately linearly with the logarithm of reflectance signal amplitude. This dependence could be reduced using a slab-based compensation algorithm (e.g., as described in S. S. Gao, Y. Jia, L. Liu, M. Zhang, H. L. Takusagawa, J. C. Morrison, and D. Huang, "Compensation for Reflectance Variation in Vessel Density Quantification by Optical Coherence Tomography Angiography," Invest Ophthalmol Vis Sci 57, 4485-4492 (2016), incorporated by reference herein) or regression-based bulk-motion subtraction algorithm (rb-BMS) (e.g., as described in A. Camino, Y. Jia, G. Liu, J. Wang, and D. Huang, "Regression-based algorithm for bulk motion subtraction in optical coherence tomography angiography," Biomed Opt Express 8, 3053-3066 (2017), incorporated by reference herein) over a wide range of signal strengths. In rb-BMS, the component of flow signal due to bulk motion can be characterized and subtracted from OCTA data to obtain cleaned flow signal that is more purely associated with blood flow. This algorithm discriminates vascular from avascular voxels after accounting for reflectance and bulk motion. However, there comes a point when the signal-to-noise ratio is too low for these compensation methods to work. This generally occurs in shadow regions, where the OCT beam is blocked by the iris (pupil edge) or other media opacities (vitreous floaters, cataracts). The shadow detection technique described herein identifies these regions and removes them from further analysis so that errors are not introduced into the evaluation of valid regions.

Pre-Processing

Retinal layer interfaces may be segmented from reflectance OCT B-scans, e.g., by a directional graph search method (e.g., as described in M. Zhang, J. Wang, A. D. Pechauer, T. S. Hwang, S. S. Gao, L. Liu, L. Liu, S. T. Bailey, D. J. Wilson, D. Huang, and Y. Jia, "Advanced image processing for optical coherence tomographic angiography of macular diseases," Biomed Opt Express 6, 4661-4675 (2015), incorporated by reference herein) incorporated in the COOL ART OCTA signal processing tool developed at the Center for Ophthalmic Optics & Lasers (COOL) lab (see FIG. 2A). The superficial vascular complex (SVC) may be defined between the ILM and 80% of the ganglion cell complex, and its maximum projection along the depth axis allowed en face visualization of the superficial retinal flow. The inner retina may be defined between the ILM and the outer boundary of the outer plexiform layer (OPL). The data in the inner and outer retina adding the choriocapillaris slabs may be used in the thresholding scheme discussed as follows.

Figure 2B:
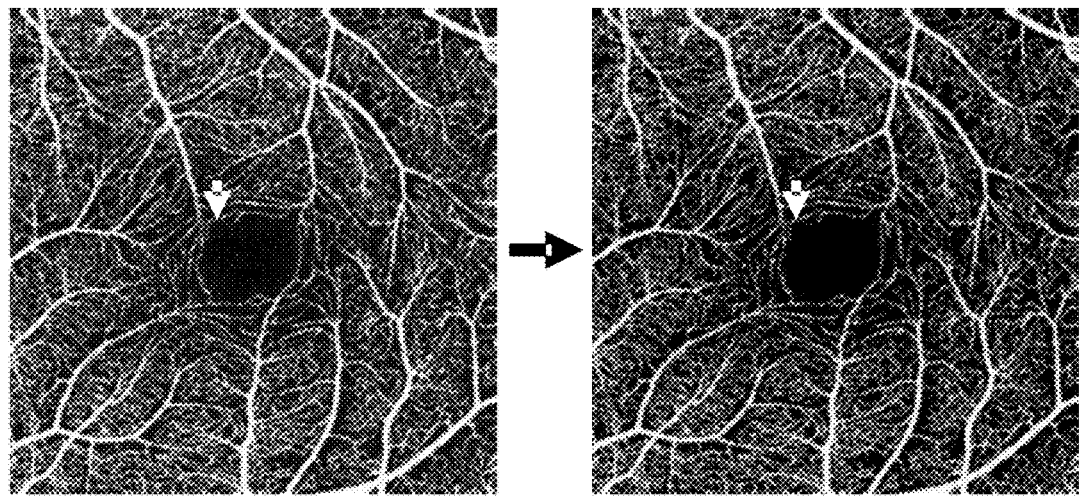

The thresholding method used in the rb-BMS algorithm may be applied to remove noise pixels in the avascular regions while preserving the vascular ones (see FIG. 2B). In some embodiments, the scans are already merged (e.g., by Optovue's registration software), and the rb-BMS method may be adapted to the data received after MCT processing. The relationship between reflectance R and bulk motion decorrelation signal $D_{BM}$ may be calculated for the pixels contained in avascular A-lines between ILM and Bruch's membrane in both the horizontal and vertical priorities. Regression analysis in this step may produce an estimate of the slope m, the intercept n and the RMS of the residual Res of the fitting data from the fitted curve. A threshold T (see Eq. (2)) may then be imposed on each voxel of the three-dimensional flow signal data to remove background signal leaving only true flow signal and their projection artifacts.

$$T(x,y,z)=mR(x,y,z)+n+2\times Res_{RMS} \qquad (2)$$

A new en face projection of the cleaned-up inner retina may be produced in which the avascular A-lines show flow signal equal to zero. The data in these avascular A-lines may be used as background reference for a second regression analysis that represents a more accurate approximation of the relationship $D_{BM}$ vs R in avascular pixels. The process may be repeated iteratively, each time for a larger proportion of the A-lines setting a larger threshold T until the percentage of vascular pixels in the en face inner-retinal angiogram reaches a plateau.

For the examples described herein, signal processing was done using MATLAB R2018a release (Mathworks, Natick, Mass., USA).

Shadow Detection

In various embodiments, scans from healthy volunteers (e.g., under optimal imaging conditions) may be used to generate position-dependent reference maps of local reflectance, local vessel density, local flow index and reflectance standard deviation. These four features were helpful to detect shadow pixels in the method for shadow detection described herein. In some embodiments, a subset or superset of these reference maps may be used for shadow detection.

In one example implementation performed by the inventors and described further herein, two 3×3 mm² and two 6×6 mm² scans of twenty healthy volunteers were obtained.

As observed in FIGS. 3A1-3A5, 3B1-3B5, and 3C1-3C5, and demonstrated in FIG. 1 as discussed above, the mean-projection commonly used for generation of en face OCT images was overwhelmed with dark structures from large superficial vessel shadows, intra-retinal fluid, soft drusen, pigment epithelium detachment or the foveal avascular zone, all of which were not related to anterior opacities. It is preferable to construct a different reflectance reference $R_{norm}$ e.g., as defined in Eq. (3):

$$R_{norm}=\max(\langle R_{scan}(x,y,z)\rangle_z)/R_{control}(x,y) \qquad (3)$$

where the mean projections of logarithmic reflectance $R_{scan}$ in both the inner (I, ILM to OPL) and the outer (O, outer retina+choriocapillaris (CC)) slabs were first normalized to the position-dependent averaged reflectance maps of the same two slabs in the healthy population ($R_{control}$) and $z\in\{I, O\}$. Then, the maximum value of the two normalized projections was used at each position to generate $R_{norm}$ (FIG. 3C1-3C5).

FIGS. 3A1-3A5, 3B1-3B5, and 3C1-3C5 illustrate support for the rationale used in the selection of $R_{norm}$ (Eq. (3)) as a feature containing information of the positions of shadows. Columns represent scans from healthy (3A1-3C1 and 3A2-3C2, also referred to as subjects #1 and #2, respectively); diabetic retinopathy (DR, 3A3-3C3 and 3A4-3C4, also referred to as subjects #3 and #4, respectively) with intra-retinal fluid; and age-related macular degeneration (AMD) with pigment epithelium detachment (PED) subjects (3A5-3C5, also referred to as subject #5). Mean projection of the OCT reflectance within the retinal slab (FIGS. 3A1-3A5) frequently shows inhomogeneous brightness, containing dark areas caused by low internal reflectance (white arrows) such as intra-retinal fluid (subjects #3 and 4) and PED (subject #5). These need to be distinguished from true shadows such as those caused by vitreous opacities (indicated by arrows). FIGS. 3B1-3B5 show representative B-scans at the positions of arrows. The corresponding $R_{norm}$ images in FIGS. 3C1-3C5) are dark only when all retinal layers are dark, which corresponds better to actual shadows.

In addition to the map $R_{norm}$, an additional feature map may be generated from the reflectance image by finding the standard deviation along the axial direction for a slab that included the retina and choriocapillaris (see FIGS. 4A-4D). This feature exploits the large variance that exists in the reflectance of retinal layers even in the presence of pathologies (e.g. FIGS. 3B3, 3B4, and 3B5)), as opposed to the tissue under shadows (e.g. FIG. 3B2) where all layers are attenuated. A map of the averaged standard deviation in the control group $$R_{std\_control}(x, y) = \frac{1}{40}\sum_{j=1}^{40} R_{std}(x, y)_j$$

may be used for normalization, generating the second feature map $R_{std\_norm}$ that is normalized to $R_{std\_control}$ and filtered (e.g., by a moving average kernel of size 9×9 pixels).

In various embodiments, additional features useful in the pixel classification task may be derived from the OCTA image. Since the OCT and OCTA images are both produced from the same optical signal, they are perfectly registered and we can further associate the position of dark areas in $R_{norm}$ and $R_{std\_norm}$ with areas of OCTA flow signal loss. In various embodiments, two additional features may be associated with shadows in OCTA.

First, the average decorrelation value of the inner retinal slab may be calculated in areas of the OCTA image (e.g., of 9×9 pixels or another suitable area), defining $FI_{focal}$ (see FIG. 5). Shadows increasingly cause filtering out of voxels with low reflectance, affecting the local flow index (FI). The local FI maps may also be normalized to the reference $FI(x,y)_{control}$ of normal subjects by Eq. (4), where D(x,y,z) is the flow signal, $\langle \ \rangle_z$ represents average over the axial dimension (z∈ILM: OPL) and $\bar{\omega}(x, y)$ is a 3×3-pixel moving average window centered at position (x, y)

$$FI_{focal}(x, y) = \frac{\langle D(x, y, z)\rangle_z \varpi(x, y)}{FI_{control}(x, y)} \quad (4)$$

One or more of the three maps described thus far ($R_{norm}$, $R_{std\_norm}$ and $FI_{focal}$) may be used as features fed to an ensemble classifier that segmented the shadow area. In addition, the supervised machine learning method may utilize a labeled training dataset. The training dataset may include data from two groups; one composed by healthy subject scans containing manufactured shadows and the other by DR scans without vitreous floaters or vignetting. Shadows appearing naturally in either healthy or diseased eyes were not used for training owing to unreliable manual assignment of labels, which will be discussed further below.

In the example depicted in FIGS. 6A1-6A2, 6B1-6B2, 6C1-6C2, and 6D1-6D2, the first group forming the training set contained the ten scans of healthy eyes with manufactured shadows of different severities. The second group consisted of 17 scans of one eye of DR subjects. This group was included in the training set with the purpose of preventing the detection of avascular areas with inherently low focal flow index and typically lower reflectance than young, healthy subjects. It should be noted that this inclusion increased the class imbalance to approximately 9-to-1, a problem that may be alleviated by choosing a random-undersampling (RUS) boost forest modality. The size of the training dataset in the example was 2.5×10⁶ vectors in feature space $\mathbb{R}^3$. Principal component analysis (PCA) may be used to investigate the feasibility of dimensionality reduction. In the example, the expressed variances were sufficiently high (66.8%, 26.8% and 6.4%) after PCA to justify the need of all dimensions in the classification routine.

Generation of Training Labels

Figures 4A, 4B, 4C, 4D:
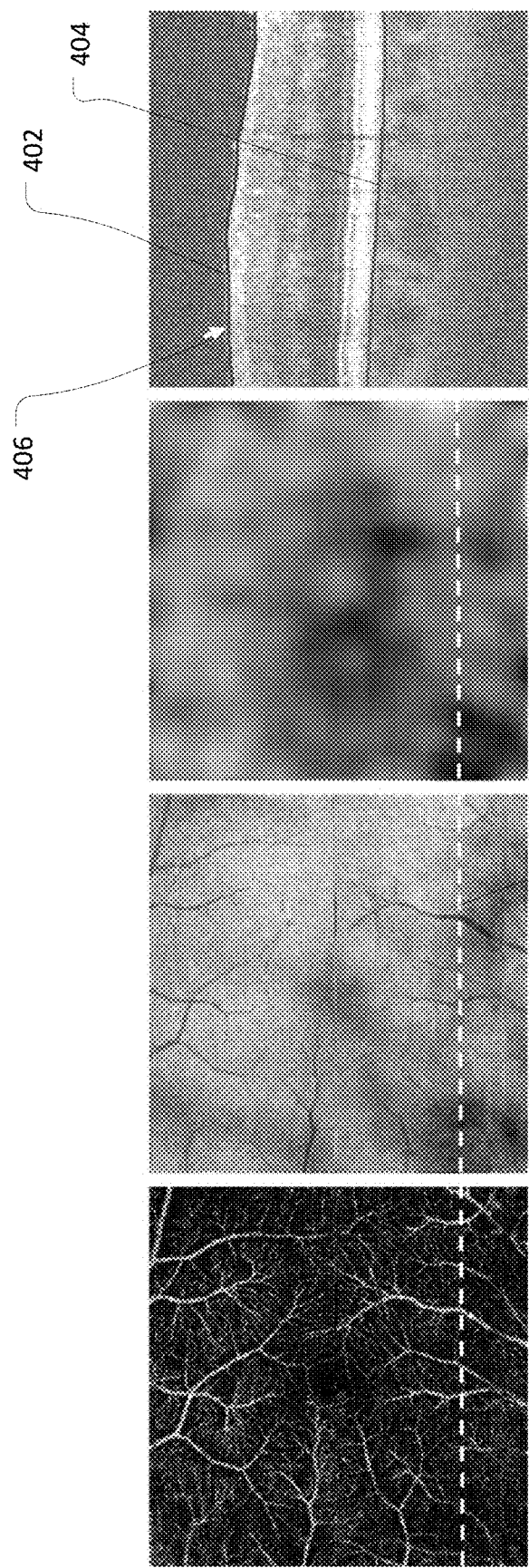
FIGS. 4A-4D illustrate the standard deviation of reflectance in shadows ($R_{std\_norm}$).

To avoid the subjectivity inherent to manual grading of shadow positions in clinical scans such as FIGS. 1A, 4A, and 5A, the method described herein is designed to label the positions of the shadows on the healthy subject scans in FIGS. 6A1-6A2, 6B1-6B2, 6C1-6C2, and 6D1-6D2. Focal vessel density maps $VD_{focal}$ may be generated by calculating the percentage of vascular pixels in respective areas (e.g., of 11×11 pixels). Rigid-body registration may be applied on scans corresponding to the same eye to overlap the center of their FAZ. Images of right eyes may be flipped before averaging in order to overlap nasal and temporal sides with equivalent local density and reflectance characteristics of left eyes.

Figures 7A, 7P:
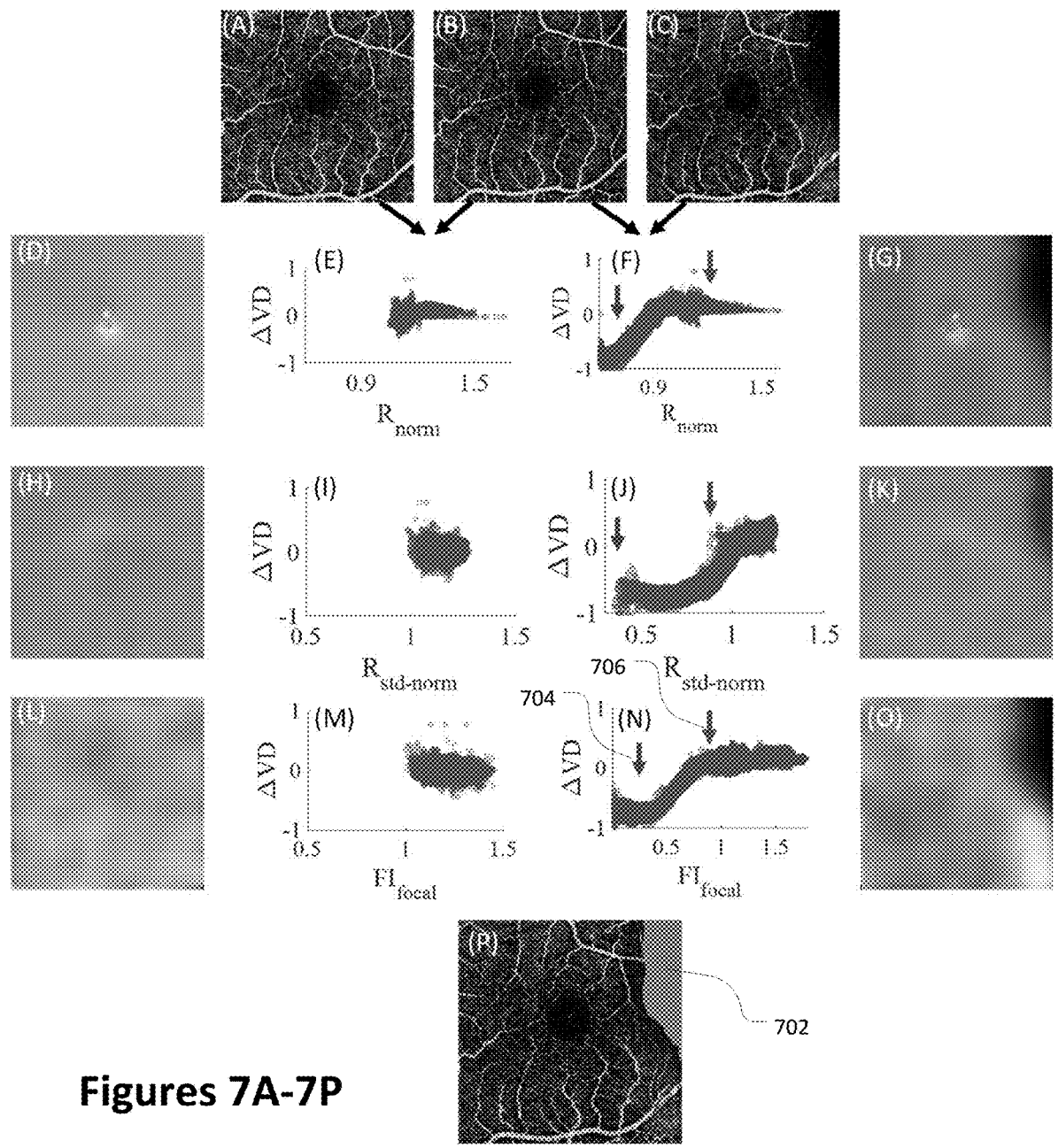
FIGS. 7A-7P illustrate a method based on statistical measures of healthy eye scans used to assign objective labels (e.g., shadow (1) vs non-shadow (0)) on the training dataset. Three scans were acquired per eye, two under optimal imaging conditions (FIGS. 7A, 7B) and one creating a manufactured shadow by partially blocking the scanning beam (FIG. 7C). Local vessel density maps VD(x,y) were generated from FIGS. 7A, 7B and 7C. The position-dependent $\Delta VD_{focal(B-A)}=VD_B(x,y)-VD_A(x,y)$ and $\Delta VD_{focal(B-C)}=VD_B(x,y)-VD_C(x,y)$ were calculated taking FIG. 7B as reference. The corresponding $\Delta VD_{focal}$ values were related to the features used by the RUS boost ensemble classifier ($R_{norm}$ in D-G, $R_{std\_norm}$ in H-K and $FI_{local}$ in L-O). Feature maps on the left (FIGS. 7D, 7H, 7L) correspond to the scan in FIG. 7A whereas the ones on the right (FIGS. 7G, 7K, 7O) correspond to the scan in FIG. 7C. $\Delta VD$ was independent from all features for the scans obtained under optimal conditions (FIGS. 7E, 7I, 7M) whereas a strong dependency was observed in the scans with manufactured shadows (red arrows 704 in FIGS. 7F, 7J, 7N). Arrows 706 in FIGS. 7F, 7J, and 7N indicate normal areas. A lower threshold set at two standard deviations of $\Delta VD_{focal(B-A)}$ was set on $\Delta VD_{focal(B-C)}$ to label the shadow points (area overlay 702 in P). Maps derived from the reflectance image were represented in grayscale whereas maps derived from the OCTA image were represented in color.

One example is illustrated in FIGS. 7A-7P. From the three scans available per subject (see FIGS. 7A-7C)) $\Delta VD_{focal}$ was found for the two scans acquired under optimal conditions (FIGS. 7A-7B) as well as between an optimal scan and a manufactured shadow (FIGS. 7B-7C). For each subject, a lower threshold was set on the shadowed scan at two standard deviations of $\Delta VD_{focal(B-A)}$ of the optimal scans and the points with $\Delta VD_{focal(B-c)}$ below threshold in the manufactured shadows were labeled with a value of 1. The remaining points were assigned a value of 0. This labeling mechanism should be more robust than manually drawing the approximate boundaries of shadows and normal areas in FIGS. 6A1-6A2, 6B1-6B2, 6C1-6C2, and 6D1-6D2 based on the subjective perception of a human grader. There was good contrast between shadow and non-shadowed regions for all three features forming the training set (see FIGS. 7D-7O)). Once the classes were assigned (see FIG. 7P), the RUS boost classifier with 100 decision trees was trained at a learning rate of 0.05. Finally, a morphological opening operation was applied to remove areas smaller than 37 connected pixels, which is the mean normal intervascular space outside the FAZ.

Software Validation

Evaluating the software performance on scans with clinical shadows is difficult because human graders cannot confidently extract its boundaries from en face images. First, as expressed above, other structures related to pathologies can contribute to darkness in the projection of reflectance and/or absence of vasculature in the projection of flow. For a human expert to generate an accurate ground truth that separates real shadows from retinal degeneration they would need to grade hundreds of reflectance B-scans per volumetric scan, while simultaneously examining those positions on en face projections of OCTA signal, which is not feasible and remains subjective. Second, as noted in Eqs. 3 and 4, the definition of shadows proposed here includes a normalization to the mean projection of a population of healthy subjects. Therefore, its classification only depends on pixel characteristics and not on a contrast between the features of pixels on both sides of the boundary. This means that in principle, in a scan significantly below the required minimum quality index (e.g. a patient with severe cataracts), the entire area could be potentially detected as a shadow, independently of whether floaters and vignetting exist or not. These cases should correspond to SSI values typically recommended for scan exclusion (e.g., SSI<55). Thus, comparison of software performance with manual grading by two experts in OCTA analysis was performed on clinical shadows of healthy subjects only, which are generally bright scans with good contrast between localized shadows and neighboring areas (e.g. FIGS. 3A2-3C2)).

In addition, the software was applied on the data acquired from the NDF experiment described above. Because scans in this experiment were acquired by attenuating the optical signal in the sample arm, some OCTA signal should be irretrievable and result in reduced apparent vessel density (percentage of vascular pixels in en face images). It was evaluated whether excluding the FAZ and the regions detected as shadows would make the vessel density of these scans independent of SSI.

Example Results

The following examples are illustrative of the disclosed methods. In light of this disclosure, those skilled in the art will recognize that variations of these examples and other examples of the disclosed methods would be possible without undue experimentation.

The algorithm was tested on a separate set of 10 healthy subjects not used in the generation of normalizing control maps. The algorithm was also run on five subjects with uveitis, five subjects with DR and one subject with AMD showing shadowed areas. In addition, three subjects with AMD and four subjects with glaucoma that did not show vitreous floaters were included with the purpose of evaluating whether retinal atrophies would cause erroneously detected shadows.

The accuracy of the RUS boost ensemble in the manufactured shadow dataset was 99.1%, the sensitivity was 93.0% and the specificity was 99.0%, evaluated by 5-fold cross-validation. For the group of clinical shadow scans the sensitivity and specificity of pixel-wise classification were 91.6% and 86.9%, taking the manual segmentation of one of the expert graders as ground truth. The other expert grader performed with a sensitivity of 87.2% and a specificity of 93.3% with respect to the same reference.

Performance on Healthy Subjects

Figures 8A, 8B, 8C, 8D:
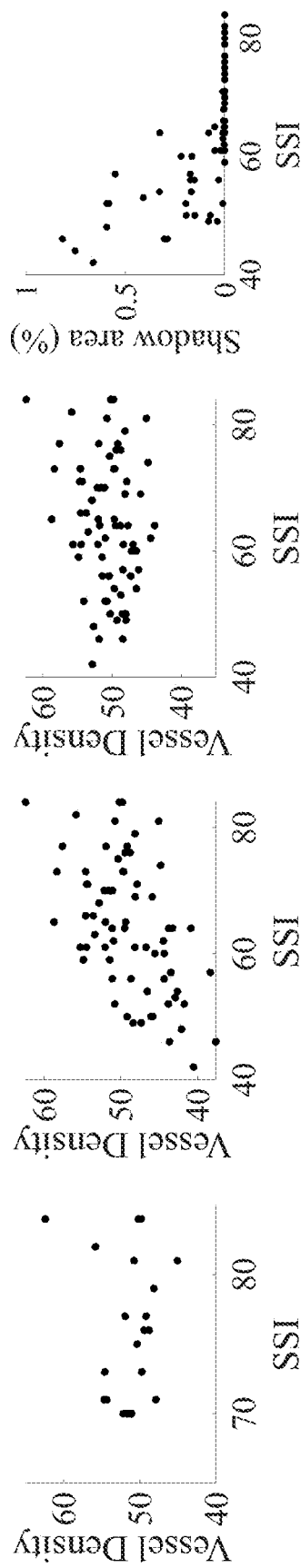
FIGS. 8A-8D illustrate performance of the shadow detection algorithm on 3×3 mm² scans of 10 healthy subjects acquired by intentionally reducing the signal strength with different combinations of neutral density filters (NDF) placed between the eye and the instrument.

The pre-processing step of vascular vs background pixel discrimination by rb-BMS successfully compensated for the dependence on reflectance on the two scans taken under optimal imaging conditions (without NDF) from healthy subjects (see FIG. 8A). The vessel density was independent from SSI (Pearson's $r=0.0669$, $p=0.77$). The repeatability between two scans on the same eye was 1.67%, evaluated by the pooled standard deviation. The mean VD was 51.4% and the standard deviation of the group was 3.6%. Noticeably, rb-BMS was unable to maintain the independence from SSI ($r=0.5220$, $p<0.01$) when part of the OCTA signal was irretrievable in scans with optical signal artificially attenuated by various combinations of NDFs (FIG. 8B). Then, by applying our shadow exclusion algorithm it was possible to retrieve areas where perfusion analysis could be considered reliable, demonstrated by the significantly reduced dependence of VD on SSI (FIG. 8(C), $r=0.1741$, $p=0.14$) and a similar VD distribution (mean=50.7%, standard deviation=3.5%) with respect to the data acquired without NDFs (FIG. 8(A)). The area of manufactured shadows formed by increasingly higher attenuation of the optical signal with NDFs was inversely proportional to the SSI (FIG. 8D).

Floaters cast by vitreous shadows and affecting clear visualization of vasculature were detected successfully on 3×3 and 6×6 mm$^2$ scans of three of the 10 healthy subjects in the test set. One representative case is shown in FIGS. 9A1-9A2, 9B1-9B2, and 9C1-9C2. En face OCT angiograms showed intact retinal vasculature after the subject had their floaters removed in a vitrectomy procedure (FIGS. 9C1-9C2). The corners of the 6×6 mm$^2$ scan were still affected by vignetting (see FIG. 9C2).

Performance on DR

Figure 10:
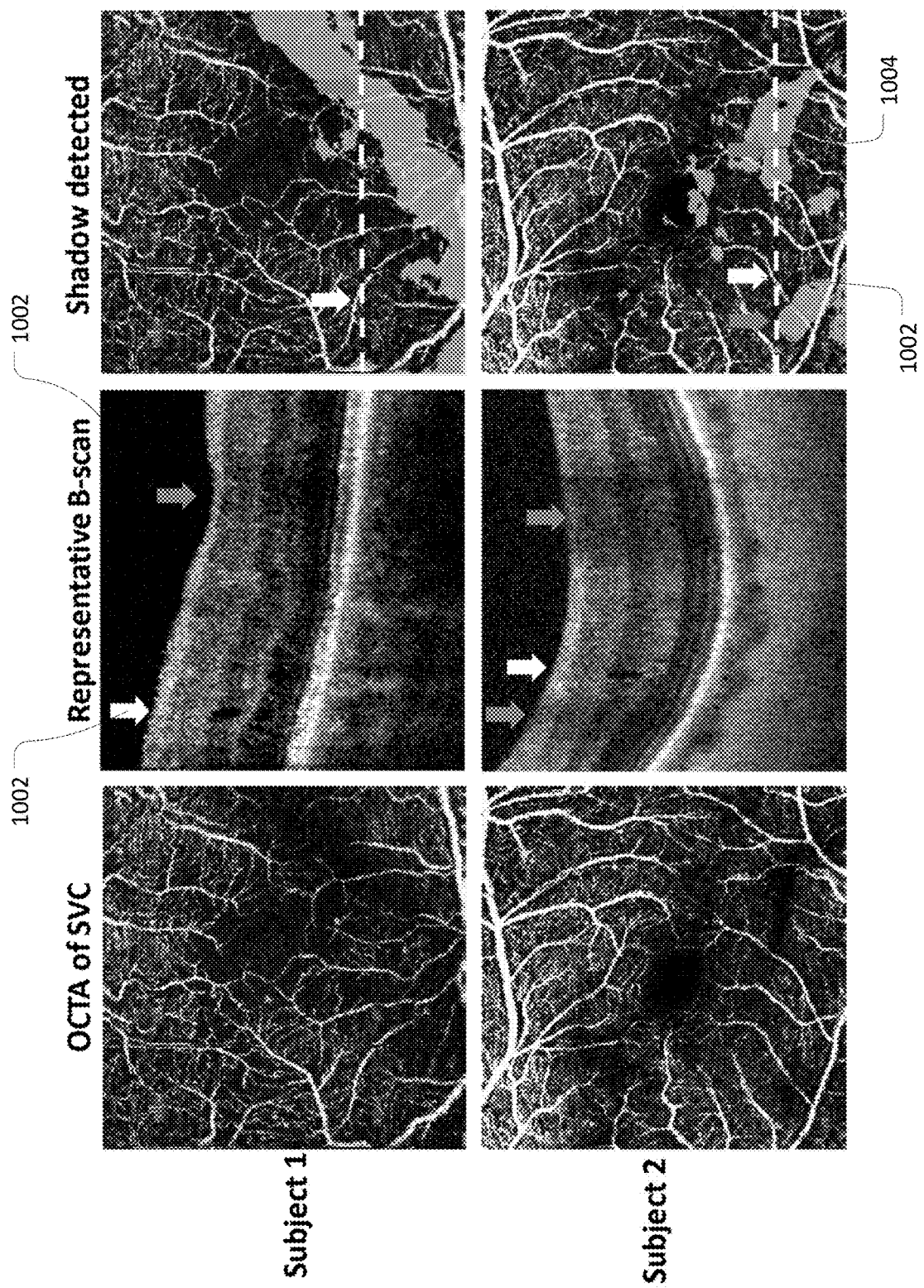
FIG. 10 illustrates areas of vitreous floater shadows detected on two DR subjects (rows). Scans comprised an area of 3×3 mm². The first column represents en face angiograms of the superficial vascular complex (SVC). The apparent loss of perfusion might be caused either by the disease or by the shadows cast by overlying vitreous floaters. The second column shows the cross-sectional view of the reflectance B-scans at the positions marked with dashed lines. Arrows 1002 represent non-shadowed areas with intraretinal fluid, whereas arrows 1004 represents shadowed areas. The third column represents the shadow area detected by the algorithm, overlaid on the en face OCT angiogram. Regions with apparent loss of perfusion outside the shadow area can be confidently measured as avascular areas.

Diabetic retinopathy patients can develop the same type of floaters that appear from normal aging but can also show additional optical signal absorption in the vitreous caused by hemorrhage from neovascular vessels in the proliferative stage of the disease. OCTA from five of the DR subjects recruited exhibited shadows from vitreous floaters in macular window of 3×3 mm$^2$ along with real avascular areas adjacent to them (see FIG. 10). These vitreous shadows were successfully detected by the algorithm.

Performance on Uveitis

Figure 11:
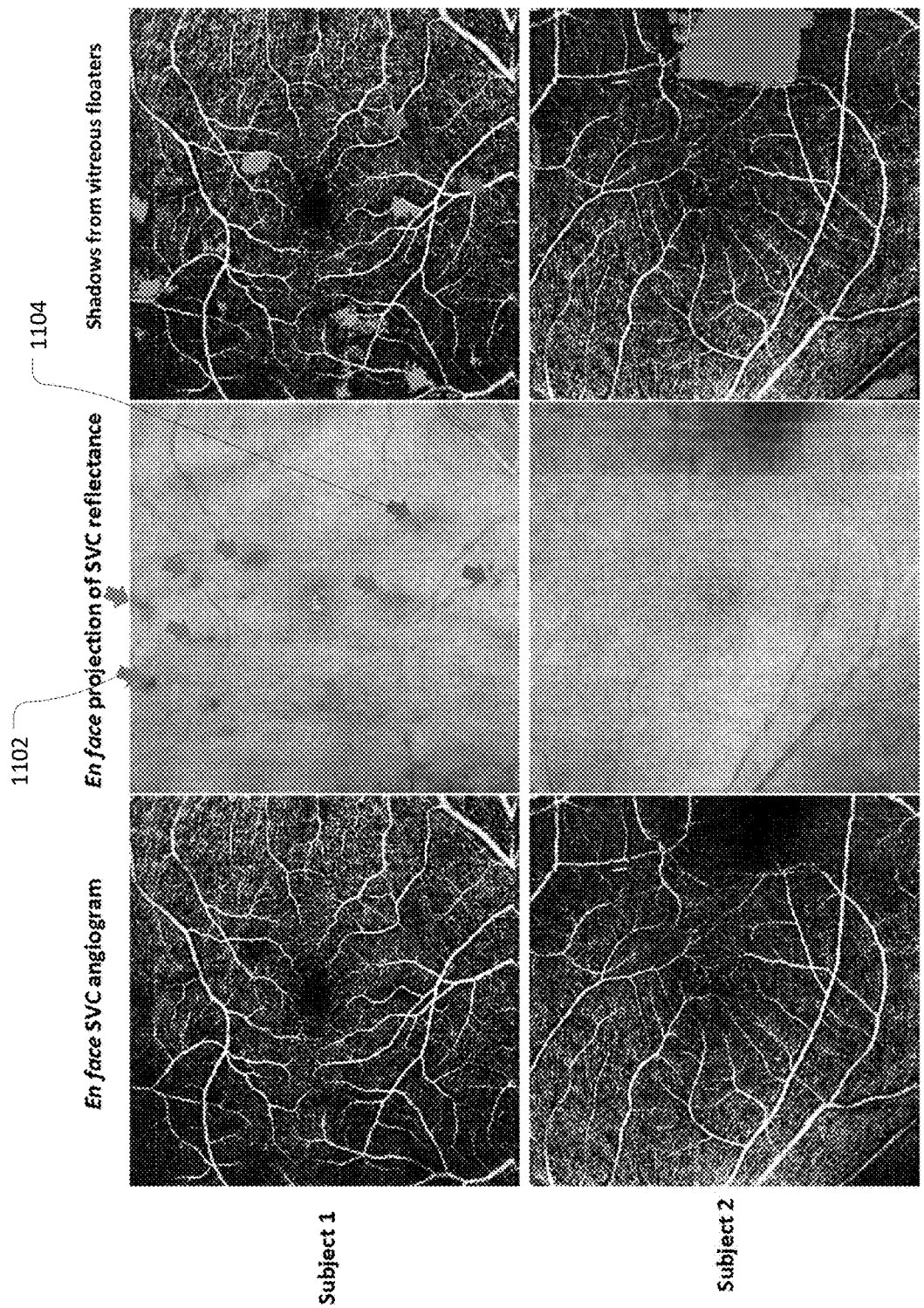
FIG. 11 illustrates areas of vitreous floater shadows detected on two uveitis subjects. En face angiograms and OCT reflectance represent an area of 6×6 mm² projected over the superficial vascular complex (SVC). Arrows 1102 represent areas with apparent loss of perfusion that were caused by shadows from either vitreous floaters (subjects 1 and 2) or pupil vignetting (subject 2) and were successfully detected by the algorithm. Arrows 1104 represent vitreous floaters that cast shadows on the reflectance projection but did not affect the angiograms and hence, were not detected. Loss of perfusion on the upper-left corner of the angiogram of subject 1 was not caused by corner vignetting and was not detected by the algorithm.

Uveitis is an inflammatory disease affecting the uvea, which comprises the iris, the ciliary body and the choroid. It can be caused by infectious, autoimmune or systemic diseases, or it could have unknown causes (white-dot syndrome). Uveitis can affect one or all of these ocular structures, but only intermediate uveitis and pan-uveitis cause inflammation of the cells in the vitreous humor, thereby creating floaters. Owing to the high prevalence of floaters, it is important in uveitis to distinguish what areas with apparent loss of perfusion represent actual capillary loss and what areas are shadows. Vitreous shadows were identified on five of the 24 subjects with uveitis participating in this study. Our algorithm proposed herein succeeded in detecting both vitreous floater shadows and vignetting in uveitis (see FIG. 11).

Performance on AMD

Figures 12A, 12B, 12C:
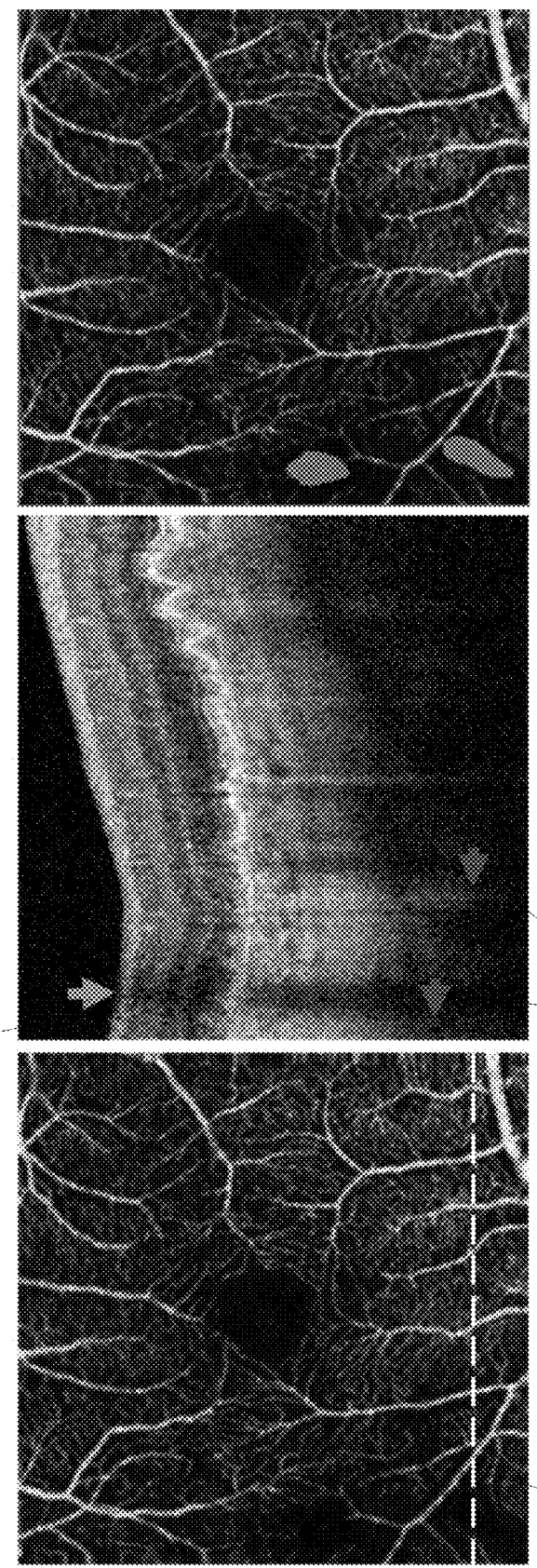
FIGS. 12A-12C depict a representative scan with drusen and RPE dystrophy showing the performance of the shadow detection algorithm described herein on one age-related macular degeneration eye. This example addresses the question of whether shadows can be detected on regions of RPE dystrophy.

Another disease in which shadow artifacts are very common is AMD because patients are elderly subjects. The high prevalence of drusen and RPE atrophies in AMD poses a special challenge to the current algorithm. In these structures, the projected reflectance values would be low due to soft drusen, pigment epithelium detachment or atrophy of the RPE layer. FIG. 12 demonstrates that the current algorithm was robust to the peculiarities of AMD, as it was able to detect shadows successfully in scans with drusen and in areas surrounded by RPE dystrophy.

Effect of MCT Registration on Shadows

Figure 13:
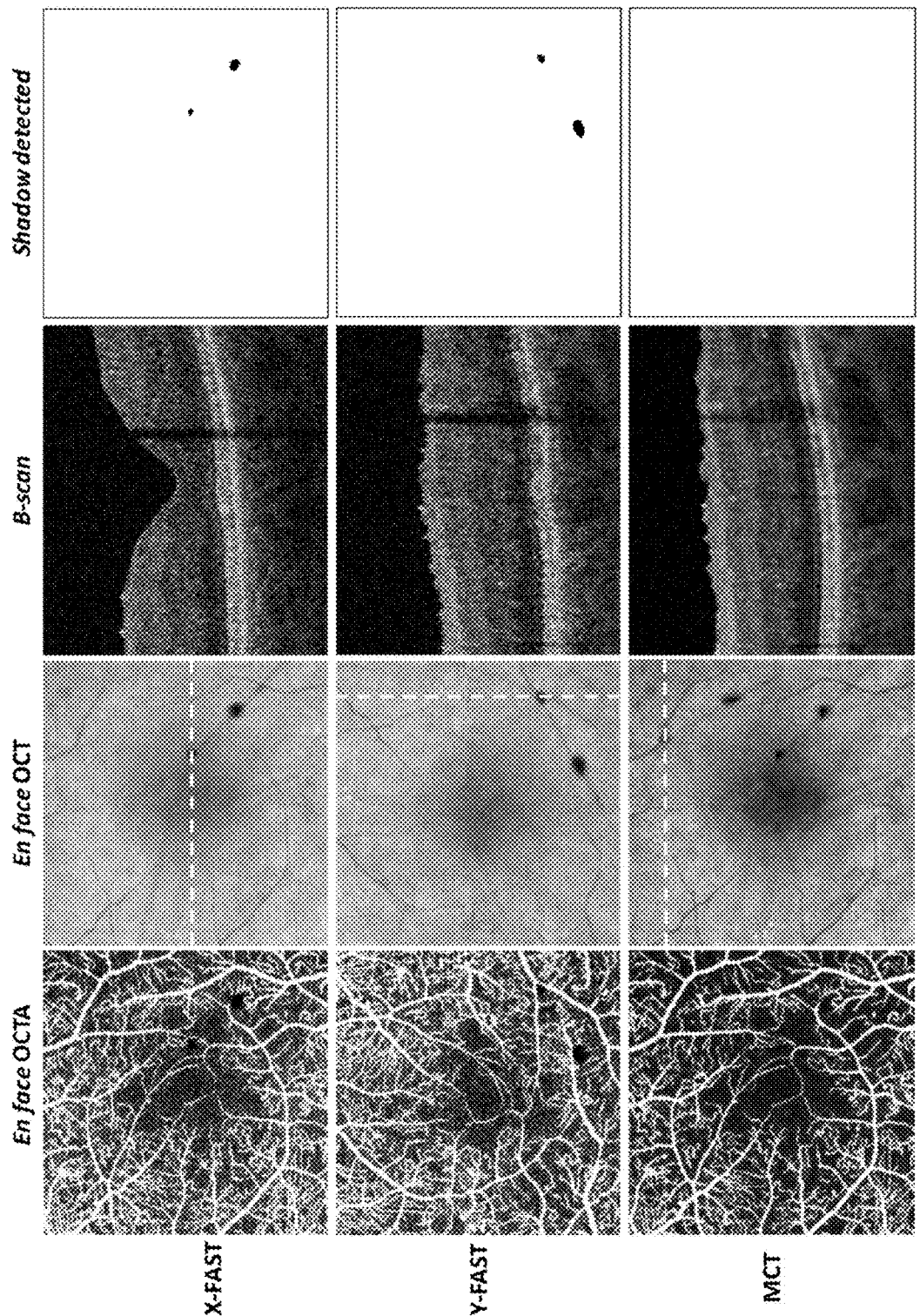
FIG. 13 illustrates the effect of motion correction technology (MCT) in shadow signal retrieval on a 3×3 mm$^2$ scan of a diabetic retinopathy subject. Dashed lines on en face OCTA and OCT views indicate the location of the cross-sectional B-scan represented in the third column. As shown in rows 1 and 2, the x-fast and y-fast scans exhibit completely loss of OCT signal under vitreous shadows. Owing to the mobility and small size of vitreous floaters, the OCTA signal could be completely retrieved by MCT in the third row.
Figure 15D:
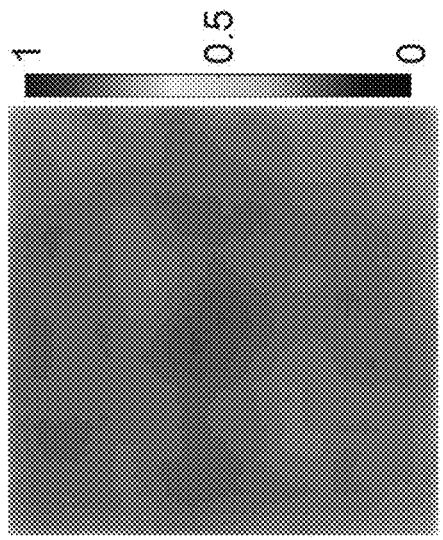
FIGS. 15A-15E illustrate generation of choriocapillaris perfusion density maps from healthy subjects.
Figure 15E:
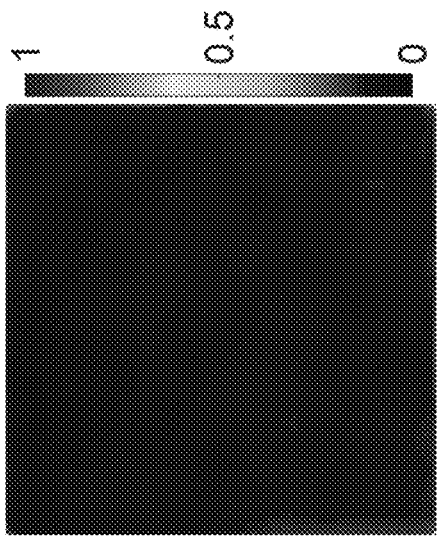
Figure 15B:
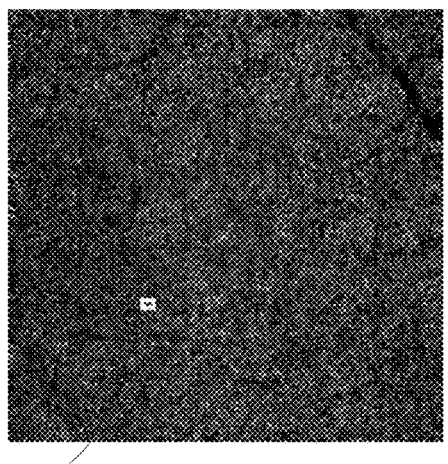
Figure 15C:
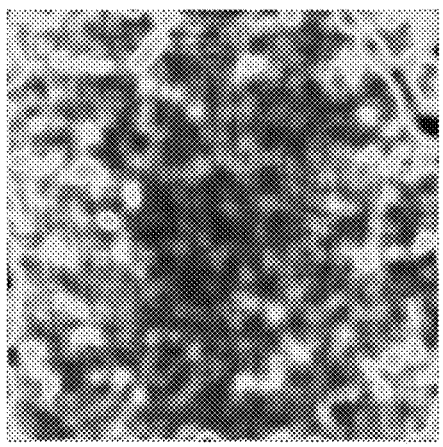
Figure 15A:
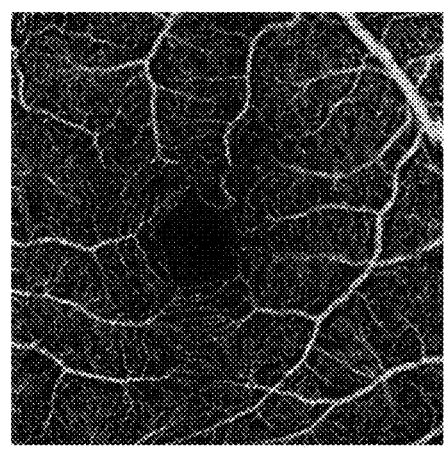
Figures 18A, 18B, 18C, 18D:
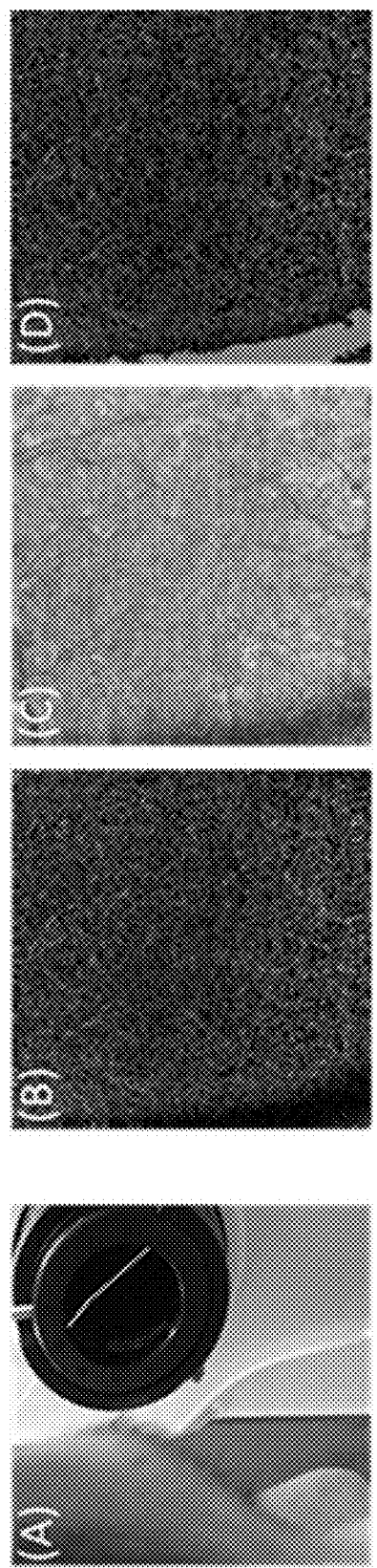
FIG. 18A illustrates artificial generation of shadows on healthy eyes to generate objective labeling of the shadow areas prior to training.
FIG. 18B is an OCTA image and FIG. 18C is an OCT image. The variation of the local vessel density of scans containing artificial shadows with respect to a scan acquired under optimal imaging conditions may be calculated and compared to the variation in local vessel density between two normal scans of the same eye. By this statistical method, the training labels may be objectively assigned to shadow positions without using subjective human judgement.
FIG. 18D illustrates the classification of shadow positions. The OCT (FIG. 18C) and OCTA (FIG. 18B) images were both useful to the subsequent classification of shadow positions in FIG. 18D.

As mentioned above, the angiographic image produced by the AngioVue instrument is generated by MCT, a software that performs the 3D registration and merging of two separate OCTA images acquired in the horizontal and vertical priority directions. While the purpose of MCT is to remove bright lines caused by microsaccadic eye motion during scanning, a side advantage is the retrieval of some OCTA data missing underneath anterior opacities (see FIG. 13). Vitreous floaters moved between the x-priority and y-priority scans owing to blinks and saccades, evidenced by the duplicated appearance of their shadows in the en face OCT image after MCT. Some OCT and OCTA signal lost in one scan (either x-fast or y-fast) could consequently be retrieved from the other if shadows did not overlap between the two scans.

Further Discussion of Retina Embodiments

In the past years, numerous clinical trials have started to exploit the potential of OCTA in detecting early changes in the diseased retina. These clinical trials rely greatly on the possibility of quantifying retinal perfusion changes by metrics such as avascular area, vessel density, flow index, FAZ acircularity, fractal dimension, among others. Artefactual shadows could obviously affect the interpretation of OCTA quantification, resulting in false diagnosis of perfusion defects or reduced capillary density. Since the flow signal cannot be computed on shadow regions, there is no way to compensate this effect; thus, these regions should be objectively detected and excluded from the quantitative measurements.

The algorithm described herein is able to detect shadows cast by vitreous floaters or pupil vignetting onto OCTA of the retina and thereby causing artefactual appearance of perfusion loss. This shadow detection algorithm is most valuable when used in conjunction with rb-BMS algorithm, which recovers vessel information in areas where shadows are not too severe. It would improve the confidence with which OCTA could be used to diagnose and evaluate a wide variety of diseases that affect the retinal circulation in the general population such as DR, AMD, glaucoma or inflammatory diseases such as uveitis. This is important as the older patient who might have these diseases also often have cataracts, vitreous opacities, small pupil, dry eye—conditions that could produce shadow artifacts that confound the real perfusion loss on OCTA in retinal and optic nerve diseases.

The shadow detection method relies on detecting the areas where shadows overlap on OCT reflectance and OCTA signals. The OCT reflectance features selected here allowed tracking areas that are dark at all retinal depths, which is rarely a manifestation of pathologies and an essential attribute of shadows. It thus helped to make the method robust to different types of retinal degenerations. They were successful in cases where the disease attacked the ganglion cell complex such as glaucoma (see FIG. 14A1-14D1) as well as in those where the outer retina and choriocapillaris are compromised, such as AMD (see FIG. 14A2-14D2).

In addition to floaters and vignetting, cataracts are also a significant source of signal loss in the aging population. The NDF experiment described above is a simulation of the effect of cataracts on signal quality. It was observed that valid areas used for vessel density measurement decreased along with the increase of the signal attenuation. This can be explained by the progressive loss of flow signal in the voxels with very low reflectance. Since all OCTA algorithms necessarily impose a reflectance threshold before generating the flow signal, the signal loss in the NDF experiment could not be entirely retrieved by rb-BMS. In cases of extreme attenuation, only the faster flow (higher decorrelation values in the nasal side of the scan) could be retrieved. Although some signal appeared to be reliable in those extreme cases, if the area excluded was too big, the analytic area might not be enough to draw useful information from the scan and it should be discarded entirely. The results in FIG. 8D appear to agree with the generally accepted signal strength standard using the SSI metric.

One limitation of the method's evaluation was the small number of subjects participating in it. Only three healthy subjects with natural floater shadows could be recruited. A second limitation was that vignetting artifacts at the corner of OCTA images were very rare in 3×3 mm² scans and only vitreous floater shadows could be studied within this field of view.

In summary, the shadow detection technique described herein is able to detect shadowed areas by anterior opacities in OCTA of the retina. The method showed good performance on 3×3 and 6×6 mm² scans of healthy, DR, AMD and uveitis cases by objectively identify shadows from vitreous floaters as well as pupil vignetting. Although these artifacts are very difficult to prevent in clinic, this software can be useful to improve the reliability of OCTA parameters by excluding shadow areas from the analysis. As the field of view available for OCTA increases over time, these shadow artifacts are expected to become more prevalent in en face images and their detection and subsequent exclusion should become even more critical.

Choriocapillaris Embodiments

As discussed above, the shadow detection techniques described herein may additionally or alternatively be applied to image the choriocapillaris. For example, a method is described herein that detects areas of choriocapillaris (CC) perfusion loss in patients with dry age-related macular degeneration (AMD) using optical coherence tomography angiography (OCTA).

In an example experiment to validate the choriocapillaris method, 3×3 mm OCTA scans were acquired by a spectral-domain OCT/OCTA system (70-kHz Avanti/AngioVue) from AMD and control subjects. Vascular voxels were identified by a thresholding method in the iterative regression-based bulk-motion subtraction (irb-BMS) algorithm that analyzed both reflectance and flow signals. Projection-resolved OCTA was used to remove projection artifacts. Shadows caused by vitreous floaters, pupil vignetting, large retinal vessels and drusen are often responsible of artefactual appearance of CC perfusion loss. A shadow-exclusion algorithm was trained using artificial shadows in normal eyes to detect the low reflectance areas with missing flow signal that could not be retrieved by irb-BMS. Drusen was detected by an automated method.

Two metrics were then used to evaluate CC perfusion. Vessel density (VD) was defined as the percentage of CC vascular pixels excluding shadowed areas. Focal perfusion loss (FPL) was calculated by integrating the loss of capillary density relative to the young normal control group within focal low perfusion areas (LPA).

For the experiment, 28 participants with intermediate AMD but no geographic atrophy (GA), 18 healthy age-matched control subjects, and 40 healthy young controls were enrolled. The shadow exclusion areas corresponded with regions of thick drusen. Calibration of the signal corresponding to shadows allowed to use a large portion of drusen in the effective analytic area, excluding areas of unreliable signal. VD was lower and FPL was higher in the AMD groups than in the age-matched control group. VD was lower under drusen than in areas with normal RPE ($p<0.05$). Univariate linear regression showed VD was negatively correlated ($p=0.05$) and FPL was positively correlated with drusen area ($p=0.04$).

As the experiment showed, Choriocapillaris FPL and VD are able to detect perfusion defects in dry AMD compared to healthy eyes. The shadow detection and exclusion algorithm allowed measurement of VD under some drusen areas.

Additional details on the choriocapillaris embodiment are described below.

Introduction on Choriocapillaris Embodiment

The early manifestations of age-related macular degeneration (AMD) can be observed in both the outer retina and choroid of elderly adults. The outer retina is crucial to maintaining visual acuity and relies primarily on the trophic support of the underlying choriocapillaris (CC). Studying the outer retina and CC in the macular area is particularly important as this region contains the largest density of cone photoreceptors. Early AMD is characterized by atrophy of the CC and accumulation of drusenoid deposits on the retinal pigment epithelium (RPE). These deposits obstruct the metabolic exchange between CC and the outer retina. The disease can further complicate into advanced, vision-threatening stages known as geographic atrophy (GA) and choroidal neovascularization (CNV).

As discussed above, OCTA is an imaging modality based on the variation of OCT signal over time, which allows depth-resolved and non-invasive imaging of the retinal and choroidal flow. Although significantly attenuated by the highly-scattering RPE layer, the OCT signal coming from the CC layer is generally enough to retrieve the blood flow information. Consequently, CC flow defects in AMD eyes have been previously identified by their reduced OCTA signal. These defects can be the result of CC atrophy (no capillaries) or flow impairment (flow speed lower than the minimum detectable value). Although the resolution of OCTA devices without adaptive optics is not sufficient to resolve either the true caliber of a single choroidal capillary or the minuscule intravascular spaces, signal defects are actually easy to resolve and measure. To date, several studies have been dedicated to quantifying their size automatically by various thresholding schemes. Despite potential clinical applications, flow defects quantification must exclude large areas of irretrievable signal owing to flow signal absorption in large retinal vessels, which are lost from the effective analytic area. In addition, OCTA signal underlying superjacent absorptive material (e.g. drusen or vitreous floaters) can be unreliable because of high attenuation of the incident light.

Various embodiments described herein provide a new method using OCTA flow signal to quantify the degree of CC damage in dry AMD, introducing a novel parameter named focal perfusion loss (FPL). In various embodiments, local density maps are generated from vascular binary maps, e.g., generated by a thresholding scheme that reduces the dependence of vascular voxel classification on both OCT signal reflectance and bulk motion OCTA signal. FPL binary maps may be generated by thresholding the local density maps. This thresholding used a reference baseline generated by data from the young, healthy control group. The method detects and excludes the areas shadowed by drusen, large retinal vessels or vitreous floaters from the analytic area. Significant differences in CC capillary density and FPL between healthy subjects and dry AMD subjects were found. This method of determining areas of abnormal CC perfusion has the potential to reveal earlier signs of anomalous CC function than conventional flow void quantification.

Study Population

Three groups were recruited at the Casey Eye Institute of Oregon Health & Science University (OHSU). The first group consisted of subjects diagnosed with dry AMD. The second consisted of age-matched healthy subjects, and the third group was of young, healthy volunteers. Subjects in the AMD group were diagnosed by color fundus photography and OCT showing evidence of drusen and no evidence of CNV. The Institutional Review Board/Ethics Committee of OHSU approved the protocol and the research adhered to the tenants of the Declaration of Helsinki.

Data Acquisition

One eye of each participant was imaged with the AngioVue (RTVue-XR, Optovue, Inc. Fremont, Calif.) spectral-domain OCT/OCTA system. Scans covered an area of 3×3 mm² centered at the fovea. Each scan consisted of two orthogonal acquisitions in horizontal and vertical priority directions registered into a single volumetric data cube by Optovue's proprietary software. The isotropic sampling density was approximately 10 μm/A-line. The real-time eye tracking system incorporated in the AngioVue machine was used to minimize the prevalence of microsaccadic artifact residuals contaminating the flow signal. Two repeated B-scans were acquired at each location. Structural OCT images were generated by averaging B-scans at the same position. Blood flow images were generated using the commercial version of split-spectrum amplitude decorrelation angiography (SSADA) algorithm, which computes the decorrelation between two consecutive structural B-scans.

Data Processing

Four retinal layer boundaries (e.g., the vitreous/inner limiting membrane (ILM), outer plexiform layer (OPL)/outer nuclear layer (ONL), inner RPE and Bruch's membrane/CC) were segmented from structural OCT B-scans by a directional graph search method. An iterative regression-based bulk motion subtraction (irb-BMS) algorithm was applied to remove the confounding contribution of ocular motion. By application of irb-BMS, non-vascular voxels in the retina and CC could be identified and removed by a thresholding scheme that sets a reflectance-adjusted threshold based on the regression analysis of background flow vs local reflectance. This algorithm operates voxel-wise in three dimensions, generating depth-resolved maps of the ocular blood flow free of bulk motion. Projection artifacts cast by inner retinal flow onto the outer retina and CC were removed by a reflectance-based projection-resolved OCTA (PR-OCTA) algorithm.

After artifacts had been removed, in situ flow at different retinal depths could be recognized. En face angiograms of the inner retinal blood flow were generated by maximum projection of the flow signal between vitreous/ILM and OPL/ONL interfaces. En face angiograms of the CC were generated by maximum projection of a slab located between 10-18 μm below the Bruch's membrane, considering the RPE-to-CC distance reported recently for the normal population.

Drusen Detection

Drusen is the main cause of shadows on the choriocapillaris slab in subjects with AMD. A previous drusen detection method was applied to AMD scans (see FIGS. 17A-17D). The method uses slabs carefully selected at certain distances from the Bruch's membrane in order to delineate the boundaries of pathological areas with minimum segmentation requirements. It can automatically detect areas of soft drusen, hard drusen and subretinal drusenoid deposits (also called pseudodrusen) but cannot differentiate between the three categories. The drusen area detected was computed and its relationship with vessel density and focal perfusion loss was investigated.

Automatic Detection of Shadows on Choriocapillaris Flow

Because the choriocapillaris layer is located below the Bruch's membrane, it is vulnerable to signal loss underneath large superficial vessels, large drusen, pupil vignetting or vitreous floaters. Before computing the CC capillary density and FPL, these shadowed areas with unreliable OCTA signal needed to be identified in order to exclude them from further analysis. The effects that optical absorption by anterior opacities have on the OCTA signal at underlying tissue are further described above with respect to the retina embodiment.

A supervised machine learning algorithm was trained to detect the shadow positions. It consisted of an ensemble learning method (RUS-Boost trees) that used features of both reflectance and flow information, which were normalized to the average of the normal population. A total of 462,080 points and their labels (shadowed vs non-shadowed) composed the training dataset. In order to generate reliable labels for the shadowed areas, we created manufactured shadows on scans of ten young, healthy subjects (age 31±4 years old) by partially blocking the scanning beam (FIGS. 18A-18D). This was done by placing a filament of polylactic acid placed between the cornea and the OCTA instrument and by reducing the diameter of an external iris that creates vignetting in the corners of images. The objective labeling of the manufactured shadow positions was done by the method described above with respect to the retina embodiment.

Choriocapillaris Focal Perfusion Loss Detection

After the data processing step, en face angiograms of the in situ CC flow showed zero value at avascular positions (FIG. 14B). Vascular binary maps of the CC were thus generated from scans of 40 young healthy eyes. Then, local density maps $D_{map}$ were generated by computing the capillary density within a surrounding 10×10-pixel area for each lateral position (FIG. 14B). An expert grader manually selected the center of the foveal avascular zone (FAZ), and all local density maps from the young, healthy group were registered by rigid translations to make their FAZ-center positions overlap.

At each position of the registered CC local density maps, the average and standard deviation of the capillary density values were used to generate reference maps $CC_{Ref}$ and $CC_{STD}$ respectively (FIG. 14C-14D). These reference maps were used to find a low perfusion area (LPA) thresholds defined by $Threshold(x,y) = CC_{Ref}(x,y) - 3.1 \times CC_{STD}(x, y)$. The reference maps were again used to further generate LPA maps after thresholding (FIGS. 16A-16D). This scheme was then applied on the same 40 scans of young, healthy subjects used to generate $CC_{Ref}$ and the average size of connected perfusion loss regions was determined in order to estimate the minimum detectable area. By this evaluation it was determined that areas smaller than 15 connected pixels should be subsequently removed from FPL masks by a morphological opening operation.

Evaluation

Two metrics may be defined to analyze CC in clinical scans. The CC capillary density is defined as the percentage of vascular pixels through the whole en face CC angiograms after the removal of projection artifacts by PR-OCTA, bulk motion artifacts by irb-BMS, and the exclusion of the shadowed areas. A second metric, the CC FPL, describes the size of the region with anomalous capillary density and is defined as:

$$FPL = \left| \frac{\iint_{LPA}(CC_{AMD}(x, y) - CC_{Ref}(x, y))dxdy}{\iint_{AA}(CC_{Ref}(x, y))dxdy} \right| \quad (1)$$

where $CC_{AMD}$ is the density map of the AMD subject under analysis and AA is the analytic area.

The relationships of drusen area with either capillary density or FPL area within the effective analytic area were investigated for AMD subjects.

A Wilcoxon rank sum test was used to evaluate the statistical significance between groups, determined by $p<0.05$.

Experimental Results

CC focal perfusion loss and capillary density were calculated for the forty young healthy eyes, the twenty-six eyes with drusen and the eighteen age-matched controls.

Shadows were detected for different absorptive elements superjacent to the choroid such as large retinal vessels (FIG. 19A1-19D1) and drusen (FIG. 19A2-19D2) where normal perfusion would be out of reach for OCTA. A large portion of the areas detected as shadows correlated spatially with large drusen height (FIGS. 20A1-20D1, 20A2-20D2, 20A3-20D3). Areas with low drusen height did not generally overlap with the shadow mask.

There was focal perfusion loss in 96% of the scans in the AMD group, 33% of the scans in the age-matched group and 12.5% in the young, healthy control group. For the subjects with FPL, the average value was larger in the AMD group compared to the age-matched and young control groups (Table 1, FIGS. 21A1-21C1, 21A2-21C2, 21A3-21C3). Although more subjects in the age-matched group had FPL, their sizes were comparable to the young, healthy group.

Table 1 below illustrates the population differences between the four groups recruited in this study (mean±standard deviation). VD of young controls was larger (P<0.01) and FPL was lower (P=0.05) than older ones. VD of AMD was larger (P<0.01) and FPL was lower (P<0.01) than age-matched controls.

TABLE 1

| Group | Age (years) | Shadow exclusion area (% area) | Vessel density (% area)* | Focal perfusion loss (a.u.)* |
|---|---|---|---|---|
| Young controls | 31 ± 5 | 0.1 ± 0.3% | 81 ± 7% | 0.01 ± 0.03 |
| Older controls | 75 ± 5 | 0.7 ± 2.0% | 69 ± 6% | 0.03 ± 0.04 |
| AMD | 81 ± 2 | 3.2 ± 3.2% | 52 ± 10% | 0.35 ± 0.21 |

Figure 22:
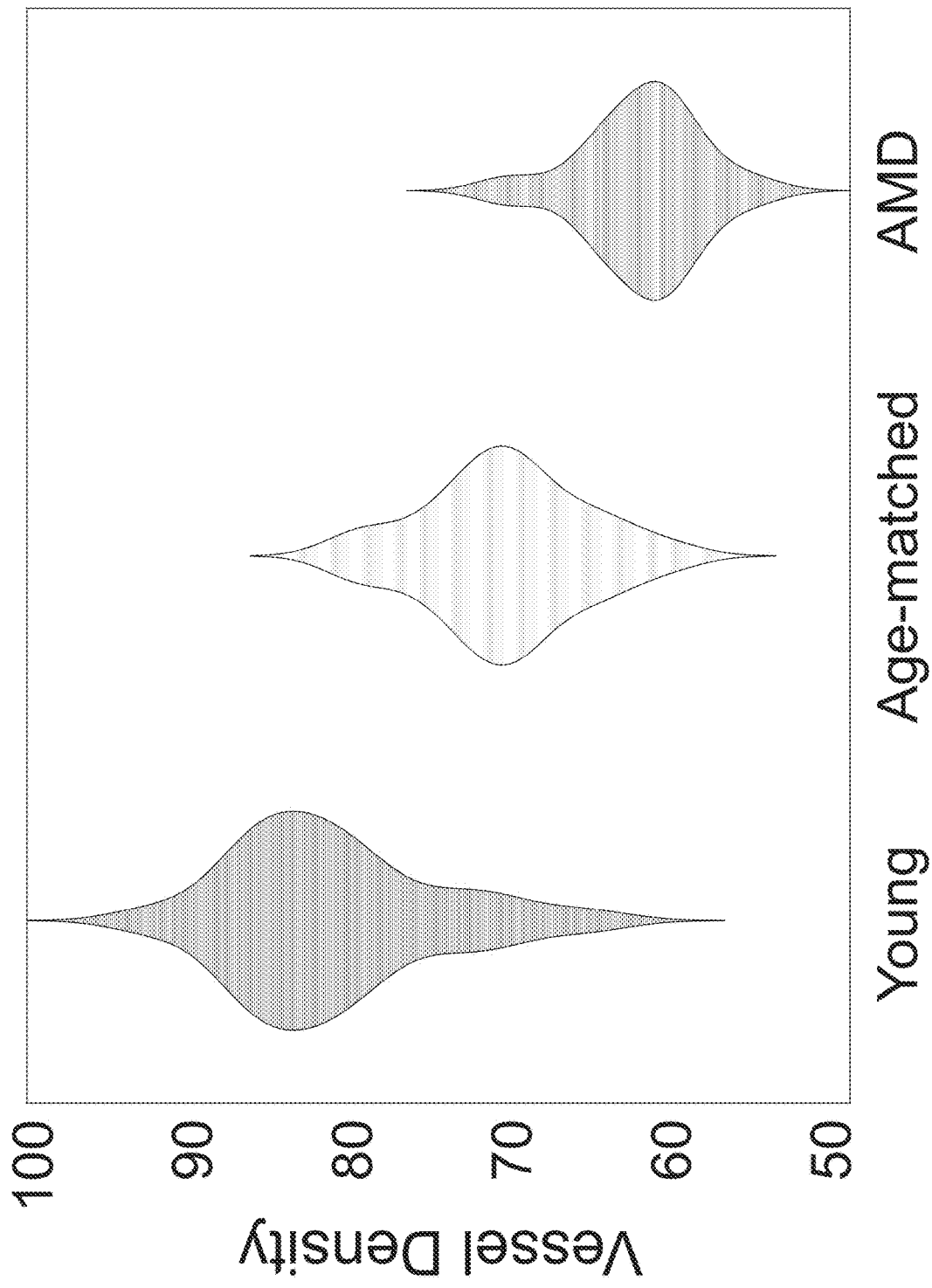
FIG. 22 illustrates violin plots of the choriocapillaris vessel density distribution of the three groups of FIGS. 21A1-21C1, 21A2-21C2, and 21A3-21C3, in accordance with various embodiments.

*Statistical significances of the differences between groups were evaluated by a Wilcoxon rank-sum test The age-related macular degeneration (AMD) group showed a significantly smaller capillary density (excluding the shadow area) than the age-matched (p<0.01) and the young (p<0.01) healthy control groups (FIG. 22). The standard deviation of the AMD group (9.5%) was larger than the age-matched (6.1%) and young (6.5%) healthy control groups. Capillary density of the young control group was also larger than the older one (p<0.05). For both healthy reference groups, the capillary density was independent from the OCT signal strength (R=−0.1351, p=0.6312, age-matched and R=0.2007, p=0.1622, young).

The drusen area of the AMD group represented 20%±14% of the scanning area. Drusen area had an inverse linear relationship with capillary density (R=−0.42, p=0.03) and a direct linear relationship with FPL (R=0.41, p=0.04), showing that although some areas contain unreliable flow signal due to shadowing, drusen has indeed a relationship with perfusion loss.

Further Discussion of Choriocapillaris Embodiment

Various embodiments herein analyze perfusion defects of the CC layer in patients with dry AMD using OCTA. Instead of finding CC flow voids by applying various thresholding mechanisms as previously used, embodiments herein find regions with abnormally low local perfusion. The associated metric called FPL relies on the local perfusion density surrounding any CC pixel (FIGS. 14A-14B) excluding those underneath shadows caused by opacities anterior to the CC layer. By this means a portion of the area under drusen is available in the effective area, thus allowing access to a larger area for CC perfusion analysis.

Although OCTA is a three-dimensional imaging technique, interaction of light with the superficial flow reproduces the vascular network onto posterior slabs, confounding the visualization of in situ flow. In various embodiments, the contribution of these projection artifacts are removed from the CC slab. OCTA is also corrupted by eye motion during acquisition which increases the signal level in background pixels. Taking measures to reduce these artifacts by image post-processing may be used to interpret the OCTA signal backscattered from the CC layer. Previously, CC capillary densities of normal population have been reported in the range of 90-99% in OCTA studies that did not make efforts to remove projection or bulk motion artifacts. In consequence, they did not quantify the CC capillary density exclusively and thus grossly overestimated its actual value. In accordance with embodiments herein, a lower density value at 80% may be obtained.

The CC consists of a very thin network of capillaries located very close to the Bruch's membrane. However, it has become a common practice to project the CC slab slightly below the anatomically correct slab, generating images formed by its projections rather than in situ flow. This attempts to attenuate the more distant retinal flow projections with respect to the more proximal CC flow projection as well as to prevent the confounding effect of amplified retinal projections that might appear in the event of layer segmentation errors. Even commercial systems have defined the choriocapillaris slab between 30-60 μm (Optovue) or 29-49 μm (Spectralis, Zeiss) below the Bruch's membrane. In embodiments herein, with the use of the PR-OCTA algorithm, the irb-BMS algorithm and the accurate layer segmentation by the graph-search method, an anatomically accurate CC slab may be visualized and a more realistic capillary density value may be quantified.

For quantification of perfusion loss the areas classified as shadows—mostly due to drusen absorption—were excluded. The problem of drusen shadowing has challenged all previous efforts attempting quantification of choroidal flow anomalies in AMD. Recently, Zhang et al compensated the CC OCTA signal attenuation by drusen absorption using the in situ OCT reflectance. In such solution overcorrection is possible and may add another type of error for CC density measurement. For instance, drusen of certain sizes may block the backscattered light to such extent that exceeds the range of retrievable CC OCTA signal. Although swept source (SS)-OCTA is known to provide better penetration than spectral domain (SD)-OCTA due to its longer wavelength and reduced sensitivity roll-off, it is still expected that some areas under large drusen would contain unreliable signal owing to excessive attenuation. Zhang et al used an empirical threshold value at less than two times the reflectance value in the FAZ region. Conversely, the shadow exclusion algorithm described and validated herein uses shadows artificially created on healthy eyes to train a machine learning classification method using objective labels.

In summary, a new method using OCTA to estimate the dimensions of the CC area affected by the progression of AMD is described herein. Two metrics, capillary density and focal perfusion loss, are investigated using in situ flow. This analysis is done after accurately removing projection, motion and shadow artifacts. The FPL metric encompasses the extent of the damage as well as the degree of flow signal reduction. Subjects with AMD exhibited lower capillary density and larger perfusion loss than young and age-matched healthy subjects. For the AMD group, drusen area had a direct relationship to loss of perfusion outside the drusen. The method used for vascular pixel discrimination was superior to thresholding for retrieving the flow signal in areas with low optical reflectivity. Accordingly, the focal perfusion loss metric described herein may identify and quantify CC regions affected by disease at an early stage of AMD disease.

Example Optical Coherence Tomography Angiography Image Processing System

Figure 23:
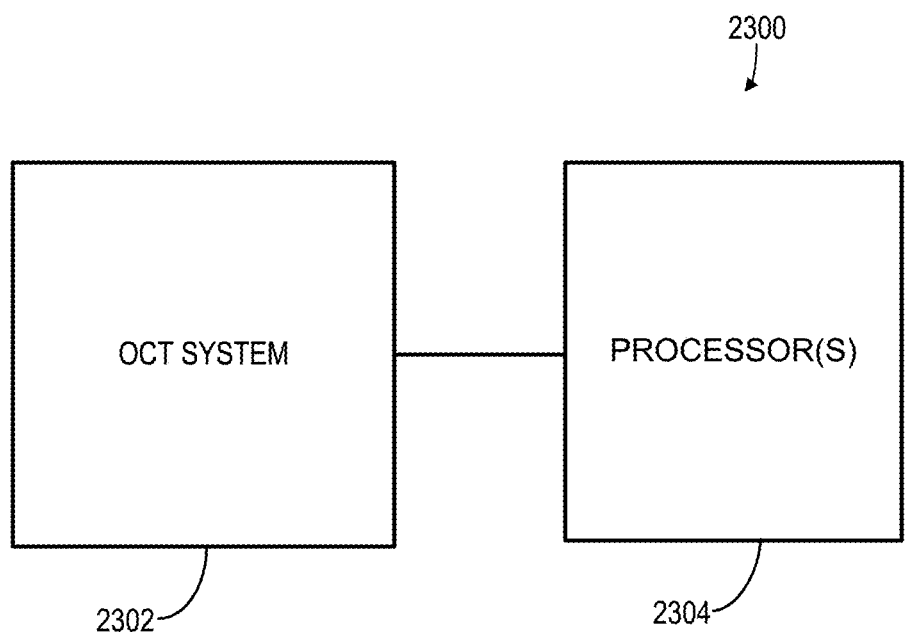
FIG. 23 schematically shows an example system for automated shadow detection in OCTA, in accordance with various embodiments.

FIG. 23 schematically shows an example system 2300 for OCT image processing in accordance with various embodiments. System 2300 comprises an OCT system 2302 configured to acquire an OCT image comprising OCT interferograms and one or more processors or computing systems 2304 that are configured to implement the various processing routines described herein. OCT system 2300 can comprise an OCT system suitable for structural OCT and OCT angiography applications, e.g., a swept source OCT system or spectral domain OCT system.

In various embodiments, an OCT system can be adapted to allow an operator to perform various tasks. For example, an OCT system can be adapted to allow an operator to configure and/or launch various ones of the methods described herein. In some embodiments, an OCT system can be adapted to generate, or cause to be generated, reports of various information including, for example, reports of the results of scans run on a sample.

In embodiments of OCT systems comprising a display device, data and/or other information can be displayed for an operator. In embodiments, a display device can be adapted to receive an input (e.g., by a touch screen, actuation of an icon, manipulation of an input device such as a joystick or knob, etc.) and the input can, in some cases, be communicated (actively and/or passively) to one or more processors. In various embodiments, data and/or information can be displayed, and an operator can input information in response thereto.

In some embodiments, the above described methods and processes can be tied to a computing system, including one or more computers. In particular, the methods and processes described herein, e.g., the methods and processes for HDR-OCTA described above, can be implemented as a computer application, computer service, computer API, computer library, and/or other computer program product.

Figure 24:
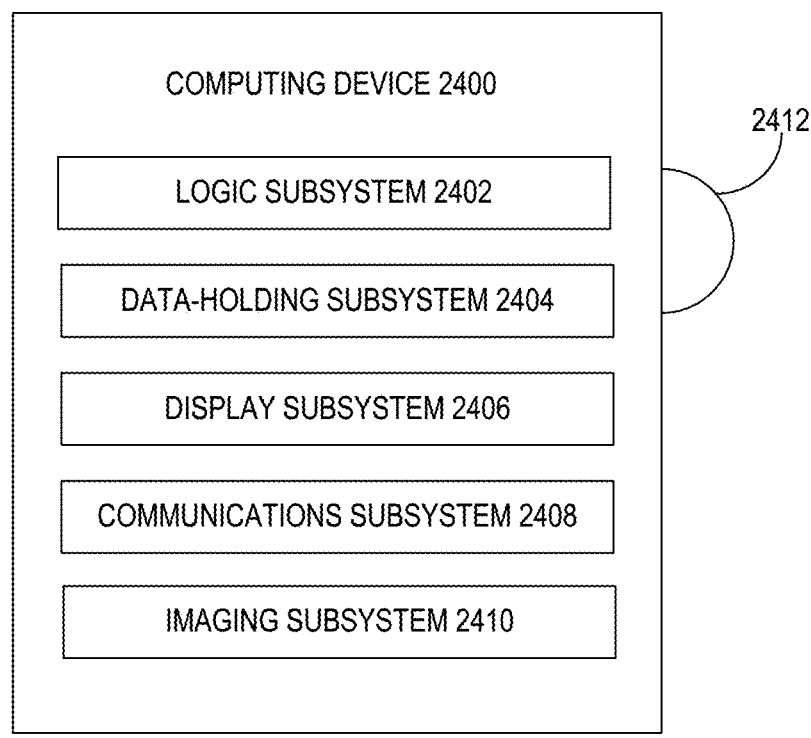
FIG. 24 schematically shows an example of a computing system in accordance with the disclosure.

FIG. 24 schematically shows a non-limiting computing device 2400 that can perform one or more of the above described methods and processes. For example, computing device 2400 can represent a processor included in system 2400 described above, and can be operatively coupled to, in communication with, or included in an OCT system or OCT image acquisition apparatus. Computing device 2400 is shown in simplified form. It is to be understood that virtually any computer architecture can be used without departing from the scope of this disclosure. In different embodiments, computing device 2400 can take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

Computing device 2400 includes a logic subsystem 2402 and a data-holding subsystem 2404. Computing device 2400 can optionally include a display subsystem 2406, a communication subsystem 2408, an imaging subsystem 2410, and/or other components not shown in FIG. 24. Computing device 2400 can also optionally include user input devices such as manually actuated buttons, switches, keyboards, mice, game controllers, cameras, microphones, and/or touch screens, for example.

Logic subsystem 2402 can include one or more physical devices configured to execute one or more machine-readable instructions. For example, the logic subsystem can be configured to execute one or more instructions that are part of one or more applications, services, programs, routines, libraries, objects, components, data structures, or other logical constructs. Such instructions can be implemented to perform a task, implement a data type, transform the state of one or more devices, or otherwise arrive at a desired result.

The logic subsystem can include one or more processors that are configured to execute software instructions. For example, the one or more processors can comprise physical circuitry programmed to perform various acts described herein. Additionally or alternatively, the logic subsystem can include one or more hardware or firmware logic machines configured to execute hardware or firmware instructions. Processors of the logic subsystem can be single core or multicore, and the programs executed thereon can be configured for parallel or distributed processing. The logic subsystem can optionally include individual components that are distributed throughout two or more devices, which can be remotely located and/or configured for coordinated processing. One or more aspects of the logic subsystem can be virtualized and executed by remotely accessible networked computing devices configured in a cloud computing configuration.

Data-holding subsystem 2404 can include one or more physical, non-transitory, devices configured to hold data and/or instructions executable by the logic subsystem to implement the herein described methods and processes. When such methods and processes are implemented, the state of data-holding subsystem 2404 can be transformed (e.g., to hold different data).

Data-holding subsystem 2404 can include removable media and/or built-in devices. Data-holding subsystem 2404 can include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 2404 can include devices with one or more of the following characteristics: volatile, nonvolatile, dynamic, static, read/write, read-only, random access, sequential access, location addressable, file addressable, and content addressable. In some embodiments, logic subsystem 2402 and data-holding subsystem 2404 can be integrated into one or more common devices, such as an application specific integrated circuit or a system on a chip.

FIG. 24 also shows an aspect of the data-holding subsystem in the form of removable computer-readable storage media 2412, which can be used to store and/or transfer data and/or instructions executable to implement the herein described methods and processes. Removable computer-readable storage media 2412 can take the form of CDs, DVDs, HD-DVDs, Blu-Ray Discs, EEPROMs, flash memory cards, USB storage devices, and/or floppy disks, among others.

When included, display subsystem 2406 can be used to present a visual representation of data held by data-holding subsystem 2404. As the herein described methods and processes change the data held by the data-holding subsystem, and thus transform the state of the data-holding subsystem, the state of display subsystem 2406 can likewise be transformed to visually represent changes in the underlying data. Display subsystem 2406 can include one or more display devices utilizing virtually any type of technology. Such display devices can be combined with logic subsystem 2402 and/or data-holding subsystem 2404 in a shared enclosure, or such display devices can be peripheral display devices.

When included, communication subsystem 2408 can be configured to communicatively couple computing device 2400 with one or more other computing devices. Communication subsystem 2408 can include wired and/or wireless communication devices compatible with one or more different communication protocols. As non-limiting examples, the communication subsystem can be configured for communication via a wireless telephone network, a wireless local area network, a wired local area network, a wireless wide area network, a wired wide area network, etc. In some embodiments, the communication subsystem can allow computing device 2400 to send and/or receive messages to and/or from other devices via a network such as the Internet.

When included, imaging subsystem 2410 can be used acquire and/or process any suitable image data from various sensors or imaging devices in communication with computing device 2400. For example, imaging subsystem 2410 can be configured to acquire OCT image data, e.g., interferograms, as part of an OCT system, e.g., OCT system 2302 described above. Imaging subsystem 2410 can be combined with logic subsystem 2402 and/or data-holding subsystem 2404 in a shared enclosure, or such imaging subsystems can comprise periphery imaging devices. Data received from the imaging subsystem can be held by data-holding subsystem 2404 and/or removable computer-readable storage media 2412, for example.

It is to be understood that the configurations and/or approaches described herein are exemplary in nature, and that these specific embodiments or examples are not to be considered in a limiting sense, because numerous variations are possible. The specific routines or methods described herein can represent one or more of any number of processing strategies. As such, various acts illustrated can be performed in the sequence illustrated, in other sequences, in parallel, or in some cases omitted. Likewise, the order of the above-described processes can be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A method for optical coherence tomography (OCT) imaging, the method comprising:
   obtaining an OCT dataset of a sample;
   obtaining an OCT angiography (OCTA) dataset from the OCT dataset;
   applying a machine-learning algorithm to the OCT dataset and the OCTA dataset to detect one or more shadow artifacts in the sample, wherein the machine-learning algorithm is trained with first training data from first training samples that include manufactured shadows and no perfusion defects and second training data from second training samples that include perfusion defects and no manufactured shadows; and
   suppressing the shadow artifacts in the OCTA dataset to generate a shadow-suppressed OCTA dataset.

2. The method of claim 1, wherein applying the machine-learning algorithm to detect the one or more shadow artifacts includes detecting the one or more shadow artifacts based on one or more feature maps of the OCT dataset and/or the OCTA dataset, wherein the one or more feature maps include on one or more of: a local reflectance feature map based on the OCT dataset, a reflectance standard deviation feature map based on the OCT dataset, a local vessel density feature map based on the OCTA dataset, or a local flow index feature map based on the OCTA dataset.

3. The method of claim 2, wherein the one or more feature maps include the local reflectance feature map, and wherein the local reflectance feature map includes normalized reflectance values based on two or more slabs of the OCT dataset that are normalized with respect to position-dependent averaged reflectance maps of an outer slab and an inner slab of a set of healthy samples.

4. The method of claim 3, wherein the one or more feature maps further include the reflectance standard deviation feature map.

5. The method of claim 1, further comprising applying a regression-based bulk motion subtraction (rb-BMS) algorithm to distinguish vascular from non-vascular voxels in the OCTA dataset prior to application of the machine-learning algorithm.

6. The method of claim 1, wherein the OCT dataset includes OCT data for retinal tissue of the sample.

7. The method of claim 1, wherein the OCT dataset includes OCT data for choriocapillaris tissue of the sample.

8. The method of claim 7, wherein the detected one or more shadow artifacts include one or more shadow artifacts caused by an opacity located at the retina of the sample.

9. The method of claim 8, wherein the opacity is associated with a drusen or a large vessel.

10. The method of claim 1, further comprising determining one or more metrics for the sample based on the shadow-suppressed OCTA dataset.

11. The method of claim 1, further comprising generating an OCTA image based on the shadow-suppressed OCTA dataset.

12. A system for optical coherence tomography (OCT) imaging, the system comprising:
an OCT system to acquire an OCT dataset for a sample;
a logic subsystem; and
a data holding subsystem comprising machine-readable instructions stored thereon that are executable by the logic subsystem to:
obtain an OCT angiography (OCTA) dataset from the OCT dataset;
apply a machine-learning algorithm to the OCT dataset and the OCTA dataset to detect one or more shadow artifacts in the sample, wherein the machine-learning algorithm is trained with first training data from first training samples that include manufactured shadows and no perfusion defects and second training data from second training samples that include perfusion defects and no manufactured shadows; and
suppress the shadow artifacts in the OCTA dataset to generate a shadow-suppressed OCTA dataset.

13. The system of claim 12, wherein application of the machine-learning algorithm to detect the one or more shadow artifacts includes to detect the one or more shadow artifacts based on one or more feature maps of the OCT dataset and/or the OCTA dataset, wherein the one or more feature maps include on one or more of: a local reflectance feature map based on the OCT dataset, a reflectance standard deviation feature map based on the OCT dataset, a local vessel density feature map based on the OCTA dataset, or a local flow index feature map based on the OCTA dataset.

14. The system of claim 13, wherein the one or more feature maps include the local reflectance feature map, and wherein the local reflectance feature map includes normalized reflectance values based on two or more slabs of the OCT dataset that are normalized with respect to position-dependent averaged reflectance maps of an outer slab and an inner slab of a set of healthy samples.

15. The system of claim 14, wherein the one or more feature maps further include the reflectance standard deviation feature map.

16. The system of claim 12, wherein the instructions are further executable by the logic subsystem to apply a regression-based bulk motion subtraction (rb-BMS) algorithm to distinguish vascular from non-vascular voxels in the OCTA dataset prior to application of the machine-learning algorithm.

17. The system of claim 12, wherein the OCT dataset includes OCT data for retinal tissue of the sample.

18. The system of claim 12, wherein the OCT dataset includes OCT data for choriocapillaris tissue of the sample.

19. The system of claim 18, wherein the detected one or more shadow artifacts include one or more shadow artifacts caused by an opacity located at the retina of the sample.

20. The system of claim 19, wherein the opacity is associated with a drusen or a large vessel.

21. The system of claim 12, wherein the instructions are further executable by the logic subsystem to determine one or more metrics for the sample based on the shadow-suppressed OCTA dataset.

22. The system of claim 12, wherein the instructions are further executable by the logic subsystem to generate an OCTA image based on the shadow-suppressed OCTA dataset.

* * * * *